(12) United States Patent
Chen

(10) Patent No.: US 6,623,947 B2
(45) Date of Patent: Sep. 23, 2003

(54) HUMAN GLUCOSE-6-PHOSPHATASE MOLECULES AND USES THEREOF

(75) Inventor: Hong Chen, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 16 days.

(21) Appl. No.: 09/874,132

(22) Filed: Jun. 4, 2001

(65) Prior Publication Data

US 2002/0037555 A1 Mar. 28, 2002

Related U.S. Application Data

(63) Continuation-in-part of application No. 09/586,511, filed on Jun. 2, 2000.

(51) Int. Cl.$^7$ ................................................. C12N 9/16
(52) U.S. Cl. ..................... 435/196; 435/320.1; 435/440; 536/23.2
(58) Field of Search .............................. 435/196, 320.1, 435/440; 536/23.2

(56) References Cited

FOREIGN PATENT DOCUMENTS

WO   WO 02/10363 A   2/2002

OTHER PUBLICATIONS

Martin, C. et al., "Cloning and Characterization of the Human and Rat Islet–specific Glucose–6–phosphatase Catalytic Subunit–related Protein (IGRP) Genes"; Journal of Biological Chemistry 276(27):25197–25207 (2001).
Database EMBL 'Online! EBI; Accession U01120, May 6, 1994 LEI, K. et al: Human glucose–6–phosphatase mRNA, complete cds. XP002196642.
Arden et al., 1999, Diabetes 48:531–542.
van de Werve, 2000, Eur. J. Biochem. 267.
GenBank Accession No. AF118762.
GenBank Accession No. AF118763.
GenBank Accession No. AF118764.
GenBank Accession No. AF118765.
GenBank Accession No. AF118766.
GenBank Accession No. Z47787.

Primary Examiner—Ponnathapura Achutamurthy
Assistant Examiner—Yong D Pak
(74) Attorney, Agent, or Firm—Millennium Pharmaceuticals, Inc.

(57) ABSTRACT

The invention provides isolated nucleic acids encoding human pancreatic islet-specific glucose-6-phosphatase proteins and nucleic acids having diagnostic, preventive, therapeutic, and other uses. These nucleic acids and proteins are useful for diagnosis, prevention, and therapy of a number of human and other animal disorders. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides, and antibodies. Diagnostic, screening, and therapeutic methods utilizing compositions of the invention are also provided. The nucleic acids and polypeptides of the present invention are useful as modulating agents in regulating a variety of cellular processes, including those which are aberrant in diabetes and other disorders associated with pancreatic dysfunction. The invention includes methods of modulating secretion of pancreatic hormones such as insulin and glucagon, and these methods can be used to alleviate disorders (e.g., diabetes and hyperinsulinemia) associated with aberrant secretion of these hormones.

8 Claims, 11 Drawing Sheets

```
AATTCGCCCT TCAGCTCCAA TTGCTCTATG TTTAGAATTG CCTCTTTTTC AAGATGGATT    60
TCCTTCACAG GAATGGAGTG CTCATAATTC AGCATTTGCA GAAGGACTAC CGAGCTTACT   120
ACACTTTTCT AAATTTTATG TCCAATGTTG GAGACCCCAG GAATATCTTT TTCATTTATT   180
TTCCACTTTG TTTTCAATTT AATCAGACAG TTGGAACCAA GATGATATGG GTAGCAGTCA   240
TTGGGGATTG GTTAAATCTT ATATTTAAAT GGATATTATT TGGTCATCGA CCTTACTGGT   300
GGGTCCAAGA AACTCAGATT TACCCAAATC ACTCAAGTCC ATGCCTTGAA CAGTTCCCTA   360
CTACATGTGA AACAGGTCCA GGAAGTCCAT CTGGCCATGC AATGGGCGCA TCCTGTGTCT   420
GGTATGTCAT GGTAACCGCT GCCCTGAGCC ACACTGTCTG TGGGATGGAT AAGTTCTCTA   480
TCACTCTGCA CAGACTGACC TGGTCATTTC TTTGGAGTGT TTTTTGGTTG ATTCAAATCA   540
GTGTCTGCAT CTCCAGAGTA TTCATAGCAA CACATTTTCC TCATCAAGTT ATTCTTGGAG   600
TAATTGGTGG CATGCTGGTG GCAGAGGCCT TTGAACACAC TCCAGGCATC CAAACGGCCA   660
GTCTGGGCAC ATACCTGAAG ACCAACCTCT TTCTCTTCCT GTTTGCAGTT GGCTTTTACC   720
TGCTTCTTAG GGTGCTCAAC ATTGACCTGC TGTGGTCCGT GCCCATAGCC AAAAAGTGGT   780
GTGCTAACCC CGACTGGATC CACATTGACA CCACGCCTTT TGCTGGACTC GTGAGAAACC   840
TTGGGGTCCT CTTTGGCTTG GGCTTTGCAA TCAACTCAGA GATGTTCCTC CTGAGCTGCC   900
GAGGGGGAAA TAACTACACA CTGAGCTTCC GGTTGCTCTG TGCCTTGACC TCATTGACAA   960
TACTGCAGCT CTACCATTTC CTCCAGATCC CGACTCACGA AGAGCATTTA TTTTATGTGC  1020
TGTCTTTTTG TAAAAGTGCA TCCATTCCCC TAACTGTGGT TGCTTTCATT CCCTACTCTG  1080
TTCATATGTT AATGAAACAA AGCGGAAAGA AGAGTCAGTA GAAAAAAAAA AAAAAAAA    1138
```

```
AATTCGCCCT TCAGCTCCAA TTGCTCTATG TTTAGAATTG CCTCTTTTTC AAGATGGATT  60
TCCTTCACAG GAATGGAGTG CTCATAATTC AGCATTTGCA GAAGGACTAC CGAGCTTACT  120
ACACTTTCT AAATTTTATG TCCAATGTTG GAGACCCCAG GAATATCTTT TTCATTTATT  180
TTCCACTTTG TTTTCAATTT AATCAGACAG TTGGAACCAA GATGATATGG GTAGCAGTCA  240
TTGGGGATTG GTTAAATCTT ATATTTAAAT GGATATTATT TGGTCATCGA CCTTACTGGT  300
GGGTCCAAGA AACTCAGATT TACCCAAATC ACTCAAGTCC ATGCCTTGAA CAGTTCCCTA  360
CTACATGTGA AACAGGTCCA GGAAGTCCAT CTGGCCATGC AATGGGCGCA TCCTGTGTCT  420
GGTATGTCAT GGTAACCGCT GCCCTGAGCC ACACTGTCTG TGGGATGGAT AAGTTCTCTA  480
TCACTCTGCA CAGACCTGAC TGGTCATTTC TTTGGAGTGT TTTTTGGTTG ATTCAAATCA  540
GTGTCTGCAT CTCCAGAGTA TTCATAGCAA CACATTTTCC TCATCAAGTT ATTCTTGGAG  600
TAATTGGTGG CATGCTGGTG GCAGAGGCCT TGAACACAC TCCAGCATC CAAACGGCCA  660
GTCTGGGCAC ATACCTGAAG ACCAACCTCT TTCTCTTCCT GTTTGCAGTT GGCTTTTACC  720
TGCTTCTTAG GGTGCTCAAC ATTGACCTGC TGTGGTCCGT GCCCATAGCC AAAAAGTGGT  780
GTGCTAACCC CGACTGGATC CACATTGACA CCACGCCTTT TGCTGGACTC GTGAGAAACC  840
TTGGGGTCCT CTTTGGCTTG GGCTTTGCAA TCAACTCAGA GATGTTCCTC CTGAGCTGCC  900
GAGGGGAAA TAACTACACA CTGAGCTTCC GGTTGCTCTG TGCCCTTGACC TCATTGACAA  960
TACTGCAGCT CTACCATTTC CTCCAGATCC CGACTCACGA AGAGCATTTA TTTTATGTGC  1020
TGTCTTTTTG TAAAAGTGCA TCCATTCCCC TAACTGTGGT TGCTTTCATT CCCTACTCTG  1080
TTCATATGTT AATGAAACAA AGCGGAAAGA AGAGTCAGTA GAAAAAAAAA AAAAAAAA    1138
```

Fig. 1

```
Met Asp Phe Leu His Arg Asn Gly Val Leu Ile Ile Gln His Leu Gln
 1                   5                      10                  15

Lys Asp Tyr Arg Ala Tyr Tyr Thr Phe Leu Asn Phe Met Ser Asn Val
                20                      25                      30

Gly Asp Pro Arg Asn Ile Phe Phe Ile Tyr Phe Pro Leu Cys Phe Gln
            35                      40                      45

Phe Asn Gln Thr Val Gly Thr Lys Met Ile Trp Val Ala Val Ile Gly
        50                      55                      60

Asp Trp Leu Asn Leu Ile Phe Lys Trp Ile Leu Phe Gly His Arg Pro
 65                     70                      75                  80

Tyr Trp Trp Val Gln Glu Thr Gln Ile Tyr Pro Asn His Ser Ser Pro
                85                      90                      95

Cys Leu Glu Gln Phe Pro Thr Thr Cys Glu Thr Gly Pro Gly Ser Pro
                100                     105                     110

Ser Gly His Ala Met Gly Ala Ser Cys Val Trp Tyr Val Met Val Thr
        115                     120                     125

Ala Ala Leu Ser His Thr Val Cys Gly Met Asp Lys Phe Ser Ile Thr
        130                     135                     140
```

Fig. 2A

```
Leu His Arg Leu Thr Trp Ser Phe Leu Trp Ser Val Phe Trp Leu Ile
145                 150                 155                 160
Gln Ile Ser Val Cys Ile Ser Arg Val Phe Ile Ala Thr His Phe Pro
                165                 170                 175
His Gln Val Ile Leu Gly Val Ile Gly Met Leu Val Ala Glu Ala
            180                 185                 190
Phe Glu His Thr Pro Gly Ile Gln Thr Ala Ser Leu Gly Thr Tyr Leu
                195                 200                 205
Lys Thr Asn Leu Phe Leu Phe Ala Val Gly Phe Tyr Leu Leu
210                 215                 220
Leu Arg Val Leu Asn Ile Asp Leu Leu Trp Ser Val Pro Ile Ala Lys
225                 230                 235                 240
Lys Trp Cys Ala Asn Pro Asp Trp Ile His Ile Asp Thr Thr Pro Phe
                245                 250                 255
Ala Gly Leu Val Arg Asn Leu Gly Val Leu Phe Gly Leu Gly Phe Ala
                260                 265                 270
Ile Asn Ser Glu Met Phe Leu Leu Ser Cys Arg Gly Gly Asn Asn Tyr
275                 280                 285
```

Fig. 2B

Thr Leu Ser Phe Arg Leu Leu Cys Ala Leu Thr Ser Leu Thr Ile Leu
290                     295                     300

Gln Leu Tyr His Phe Leu Gln Ile Pro Thr His Glu Glu His Leu Phe
305                     310                     315                 320

Tyr Val Leu Ser Phe Cys Lys Ser Ala Ser Ile Pro Leu Thr Val Val
                        325                     330                 335

Ala Phe Ile Pro Tyr Ser Val His Met Leu Met Lys Gln Ser Gly Lys
                    340                     345                 350

Lys Ser Gln
355

Fig. 2C

```
H   1  MDFLHRNGVLIIQHLQKDYRAYYTFLNFMSNVGDPRNIFFIYFPLCFQFN
M   1  MDFLHRSGVLIIHHLQEDYRTYYGFLNFMSNVGDPRNIFSIYFPLWFQLN

H  51  QTVGTKMIWVAVIGDWLNLIFKWILFGHRPYWWVQETQIYPNHSSPCLEQ
M  51  QNVGTKMIWVAVIGDWFNLIFKWILFGHRPYWWIQETEIYPNHSSPCLEQ

H 101  FPTTCETGPGSPSGHAMGASCVWYVMVTAALSHTVCGMDKFSITLHRLTW
M 101  FPTTCETGPGSPSGHAMGSSCVWYVMVTAALSYTISRMEESSVTLHRLTW

H 151  SFLWSVFWLIQISVCISRVFIATHFPHQVILGVIGGMLVAEAFEHTPGIQ
M 151  SFLWSVFWLIQISVCISRVFIATHFPHQVILGVIGGMLVAEAFEHTPGVH

H 201  TASLGTYLKTNLFLFLFAVGFYLLLRVLNIDLLWSVPIAKKWCANPDWIH
M 201  MASLSVYLKTNVFLFLFALGFYLLLRLFGIDLLWSVPIAKKWCANPDWIH

H 251  IDTTPFAGLVRNLGVLFGLGFAINSEMFLLSCRGGNNYTLSFRLLCALTS
M 251  IDSTPFAGLVRNLGVLFGLGFAINSEMFLRSCQGENGTKPSFRLLCALTS
```

Fig. 3A

```
H 301  LTILQLYHFLQIPTHEEHLFYVLSFCKSASIPLTVVAFIPYSVHMLMKQS
       ||  :||—|||——|||— — |||•||——|||||||||  ||| ||| |||||:
M 301  LTTMQLYRFIKIPTHAEPLFYLLSFCKSASIPLMVVALIPYCVHMLMRPG

H 351  GKKSQ
       ||••·
M 351  DKKTK
```

Fig. 3B

```
Hp  MDFLHRNGVLIIQHLQKDYRAYYTFLNFMSNVGDPRNIFFIYFPLCFQFN
Mp  MDFLHRSGVLIIHHLQEDYRTYYGFLNFMSNVGDPRNIFSIYFPLWFQLN
Fl  MDLLHSWGVELAVYLQTRYGKYEGLFDLASTVADLHTTFFWLFPIWFHLR
Ml  MEEGMNILHDFGIQSTRYLQVNYQDSQDWFILVSVIADLRNAFYVLFPIWFHLK
Cl  MEKGMDVLHDFGIQSTHYLQVNYQDSQDWFILVSVIADLRNAFYVLFPIWFHLR
Hl  MEEGMNVLHDFGIQSTHYLQVNYQDSQDWFILVSVIADLRNAFYVLFPIWFHLQ

Hp  QTVGTKMIWVAVIGDWLNLIFGHRPYWWVQETQIYPNHSSPCLEQFPTT
Mp  QNVGTKMIWVAVIGDWFNLIFKWILFGHRPYWWIQETEIYPNHSSPCLEQFPTT
Fl  RDTALRLIWVAVIGDWLNLVLKWVLFGERPYWWVHETKFYGAGPAPSLQQFPIT
Ml  ETVGINLLWVAVVGDWENLVFKWILFGQRPYWWVLDTDYSNSSVPIIKQFPVT
Cl  EAVGIKLLWVAVIGDWLNLVFKWILFGQRPYWWVMDTDYSNTSVPLIKQFPVT
Hl  EAVGIKLLWVAVIGDWLNLVFKWILFGQRPYWWVLDTDYYSNTSVPLIKQFPVT

Hp  CETGPGSPSGHAMGASCVWYVMVTAALSHTVCGMDKFSITLHRLTWSFLWSVFW
Mp  CETGPGSPSGHAMGSSCVWYVMVTAALSYTISRMEESSVTLHRLTWSFLWSVFW
Fl  CETGPGSPSGHAMGAAGVWYVMVTALLS---IAREKQCPPLLYRFLYIGLWMLMG
Ml  CETGPGSPSGHAMGAAGVYYVMVTSTLA---IFRGKKKPTYGFRCLNVILWLGFW
Cl  CETGPGSPSGHAMGTAGVYYYVMVTSTLS---IFRGRKRPTYRFRCLNILLWLGFW
Hl  CETGPGSPSGHAMGTAGVYYYVMVTSTLS---IFQGKIKPTYRFRCLNVILWLGFW
```

Fig. 6A

```
Hp  LIQISVCISRVFIATHFPHQVILGVIGGMLVAEAFEHTPGIQTASLGTYLKTNL
Mp  LIQISVCISRVFIATHFPHQVILGVIGGMLVAEAFEHTPGVHMASLSVYLKTNV
Fl  LVELVVCISRVYMAAHFPHQVIAGIITGTLVAEVVSKEKWIYSASLKKYFLITL
Ml  AVQLNVCLSRIYLAAHFPHQVVAGVLSGIAVAETFSHIRGIYNASLRKYCLITI
Cl  AVQLNVCLSRIYLAAHFPHQVVAGVLSGIAVAETFRHIQSIYNASLKKYFLITF
Hl  AVQLNVCLSRIYLAAHFPHQVVAGVLSGIAVTETFSHIHSIYNASLKKYFLITF

Hp  FLFLFAVGFYLLLRVLNIDLLWSVPIAKKWCANPDWIHIDTTPFAGLVRNLGVL
Mp  FLFLFALGFYLLLRLFGIDLLWSVPIAKKWCANPDWIHIDSTPFAGLVRNLGVL
Fl  FLTSFAVGFYVLLKALDVDLLWTMEKAQKWCIRPEWVHLDSAPFASLLRNMGSL
Ml  FLFGFALGFYLLLKGLGVDLLWTLEKAKRWCERPEWVHLDTTPFASLFKNLGTL
Cl  FLFSFAIGFYLLLKGLGVDLLWTLEKARRWCERPEWVHIDTTPFASLLKNVGTL
Hl  FLFSFAIGFYLLLKGLGVDLLWTLEKAQRWCEQPEWVHIDTTPFASLLKNLGTL

Hp  FGLGFAINSEMFLLSCRGGNNYTLSFRLLCALTSLTILQLYHFLQIPTHEEHLF
Mp  FGLGFAINSEMFLRSCQGENGTKPSFRLLCALTSLTTMQLYRFIKIPTHAEPLF
Fl  FGLGLGLHSPFYKTTKMRIMSA--PLRIGCIVISVSLLHLLDGWTFSPENHMTF
Ml  LGLGLALNSSMYRKSCKGELSKSFPFRFACIVASLVLLHLFDSLKPPSQVELIF
Cl  FGLGVTLNSSMYRESCKGKLSKWFPFFRLSCIVVSLILLHLFDSLKPPSQTELIF
Hl  FGLGLALNSSMYRESCKGKLSKWLPFFRLSSIVASLVLLHVFDSLKPPSQVELVF
```

Fig. 6B

```
Hp  YVLSFCKSASIPLTVVAFIPYSV-HMLMKQSGKKSQ
Mp  YLLSFCKSASIPLMVVALIPYCV-HMLMRPGDKKTK
Fl  YALSFGKSAVALLIPTTLVPWALSKIYPVKTEGKNL
Ml  YILSFCKSATVPFASVSLIPYCLARILG-QTHKKSL
Cl  YTLSFCKSAAVPLASVSLIPYCLARVFD-QPDKKSL
Hl  YVLSFCKSAVVPLASVSVIPYCLAQVLG-QPHKKSL
```

Fig. 6C

HUMAN GLUCOSE-6-PHOSPHATASE MOLECULES AND USES THEREOF

CROSS-REFERENCE TO RELATED APPLICATIONS

This application is a continuation-in-part of U.S. application Ser. No. 09/586,511, filed on Jun. 2, 2000.

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

Glucose-6-phosphatase (G6Pase; EC 3.1.3.9) catalyzes hydrolysis of glucose-6-phosphate (G6P), yielding glucose. This reaction is the terminal step in the gluconeogenic and glycogenolytic pathways.

Most cells of the body are able to convert glucose absorbed from the blood stream to G6P, thereby preventing facilitated diffusion of the glucose moiety out of the cell. Some cells, such as liver cells, possess G6Pase activity, whereby G6P can be converted to glucose and released to the bloodstream or used by the cell for metabolism. For example, formation of glucose in the liver from hepatically-stored glycogen (i.e., involving intermediate hydrolysis of G6P by G6Pase) is an important mechanism by which blood glucose is maintained at a normal level between meals.

Maintenance of normal blood glucose levels is important for nutrition of certain tissues (e.g., brain and other nervous system tissues and gonadal germinal epithelium) which are substantially incapable of metabolizing other energy sources such as fatty acids or amino acids. Lipid and protein metabolism can be undesirable, in that such metabolism depletes bodily stores of lipids and proteins, and in that the by-products of such metabolism (e.g., certain lipoprotein-containing particles) can cause or contribute to pathological conditions (e.g., deposition of lipoprotein plaque in arteries). Thus, in addition to providing nutrition to tissues which metabolize glucose almost exclusively, maintenance of normal blood glucose levels prevents physiologically inappropriate reliance of the body on non-carbohydrate catabolic routes.

In diabetic patients, in whom aberrantly diminished secretion of insulin leads to defects in carbohydrate metabolism, fat metabolism is abnormally increased, leading to greater-than-normal levels of circulating fatty acids, which in turn cause greater-than-normal deposition of cholesterol and other plaque materials in arteries. Indeed, abnormalities in fat and protein metabolism are common in diabetics, and account for much of the morbidity and mortality experienced by such patients, including acidosis, arteriosclerosis, coronary artery disease and other circulatory disorders, and wasting disease conditions (i.e., attributable to aberrant protein degradation).

In normal patients, blood insulin level during fasting is relatively constant, but increases in a two-stage manner upon influx of glucose, certain amino acids (e.g., lysine, arginine, and alanine), or particularly both, into the blood stream. A rapid increase in insulin, attributable to release of pre-formed insulin stored in secretory granules of pancreas islet of Langerhans beta cells occurs in the first stage, followed by more gradual and pronounced release of pre-sumably newly-synthesized insulin in a second stage. Secretion of glucagon, a hormone secreted by alpha cells of pancreas islet of Langerhans, is also closely regulated in coordination with blood levels of glucose and amino acids.

Although it is known that secretion of insulin and secretion of glucagon are tightly regulated, and that modulation of secretion of these molecules occurs rapidly, the mechanisms by which such secretions are modulated are not fully understood. More particularly, the mechanism by which blood glucose level, blood amino acid levels, or both, affect production, processing, and release of hormones like insulin and glucagon has not been fully elucidated. Further knowledge of the physiological mechanisms by which these processes are regulated would enable medical practitioners to more predictably and efficaciously prognosticate, diagnose, inhibit, prevent, alleviate, or even cure both hormone-associated metabolic disorders (e.g., diabetes and hyperinsulinism) and undesirable physiological phenomena (e.g. atherosclerosis, tissue wasting) that accompany such disorders.

Previously characterized G6Pase enzymes isolated from liver and kidney tissues are believed to be localized at the membrane of the endoplasmic reticulum (Ebert et al., 1999, Diabetes 48:543–554; Burchell, 1990, FASEB J. 4:2978–2988; Mithieux, 1997, Eur. J. Endocrinol. 136:137–145; Foster et al., 1997, Proc. Soc. Exp. Biol. Med. 215:314–332) and are also believed to be associated with one or more proteins which facilitate transmembrane transport of glucose-6-phostphate, glucose, or both (Gerin et al., 1997, FEBS Lett. 419:235–238; Waddell et al., 1992, Biochem. J. 286:173–177). Genes encoding G6Pase enzymes and catalytic subunits thereof have been cloned in humans and mice (Lei et al., 1993, Science 262:580–583; Shelly et al., 1993, J. Biol. Chem. 268:21482–21485). Pancreatic G6Pase is distinct from the hepatic and kidney forms of this enzyme, and has been described as being present in the endoplasmic reticulum of murine pancreatic islet of Langerhans cells of the alpha and beta types, likely in the form of a multi-protein complex. (Arden et al., 1999, Diabetes 48:531–542; Trinh et al., 1997, J. Biol. Chem. 272:24837–24842).

Human pancreatic G6Pase has not previously been isolated, nor has its sequence been determined. G6Pase activity has been reported in pancreatic islet cells (Ashcroft et al., 1968, Nature 219:857–858; Waddell et al, 1988, Biochem. J. 255:471–476). However, what, if any, role the pancreatic form of this enzyme might have physiologically was not known. A need remains for isolation and sequencing of the human gene encoding the catalytic subunit of human pancreatic islet cell-specific G6Pase. The present invention satisfies this need.

SUMMARY OF THE INVENTION

The present invention is based, at least in part, on the discovery of a cDNA molecule encoding the catalytic subunit of human pancreatic islet cell-specific G6Pase. This protein and fragments, derivatives, and variants thereof are collectively referred to as polypeptides of the invention or proteins of the invention. Nucleic acid molecules encoding polypeptides of the invention are among those collectively referred to as nucleic acid molecules of the invention.

Polypeptides of the invention include the catalytic subunit of human pancreatic islet cell-specific G6Pase ("h-ig6p") and proteins which exhibit significant homology therewith (i.e., proteins having an amino acid sequence that is at least 85%, 90%, 95%, 98%, or 99% or more identical to SEQ ID NO: 3). Other polypeptides of the invention include those which comprise (or consist of) a biologically active portion of h-ig6p (e.g., a portion which exhibits a catalytic activity of h-ig6p), a structural feature (e.g., an epitope or secondary structural domain) of h-ig6p, a functional portion of h-ig6p (e.g., a portion which binds a physiological substrate), or some combination of these.

Nucleic acid molecules of the invention include those which encode any of the polypeptides of the invention (e.g., a nucleic acid molecule that encodes the entire catalytic subunit of human pancreatic islet cell-specific G6Pase). By way of example, such nucleic acid molecules can have a nucleotide sequence that comprises (or consists of) all, or a portion, of one of SEQ ID NO: 1, SEQ ID NO: 2, and the nucleotide sequence of the clone deposited with ATCC® on Jul. 28, 2000 as accession number PTA-2282, or a complement of one of these sequences. Nucleic acids of the invention can, alternatively, have a nucleotide sequence that is at least 91% (or 92%, 95%, 98%, or 99% or more) identical to one of these sequences, particularly where the sequence identity is such that some or all of the amino acid residues described herein as having structural, functional, or catalytic relevance are preserved.

The invention also includes nucleic acid molecules which do not necessarily encode a polypeptide of the invention, but which are nonetheless suitable, for example, as a hybridization probe for detection of a nucleic acid encoding a polypeptide of the invention or as a primer for amplifying (or replicating) all or a portion of such a nucleic acid.

Also included within the scope of the invention are modulators of polypeptides and nucleic acid molecules of the invention and methods for making and identifying such modulators. Examples of such modulators include antibodies which bind specifically with h-ig6p (i.e., with an epitope of h-ig6p) and h-ig6p-binding fragments of such antibodies. Other examples of modulators of the invention include anti-sense nucleic acid molecules which are capable of hybridizing with a nucleic acid molecule of the invention (particularly including those which hybridize under stringent binding conditions) and inhibiting (or even preventing) expression thereof.

The nucleic acid molecules, polypeptides, and modulators of the invention are useful as modulating agents for regulating a variety of cellular processes, particularly including cellular processes which occur in human pancreatic islet of Langerhans cells (e.g., in alpha cells, in beta cells, or both). Examples of these cellular processes include interaction of blood glucose with alpha and beta cells and sub-cellar components thereof, secretion of insulin by beta cells, secretion of glucagon by alpha cells, and transmembrane transport of glucose (optionally coupled with phosphorylation of glucose) or of G6P (optionally coupled with de-phosphorylation of G6P) by alpha or beta cells of the pancreas. The membrane across which the hormone is transported can be, for example, the cytoplasmic membrane or the membrane surrounding the endoplasmic reticulum. These cellular processes are involved in homeostasis in humans not afflicted with a pancreatic disorder, and can also be involved in development or manifestation of a pancreatic disease state.

The invention thus includes methods of inhibiting, preventing, prognosticating, diagnosing, or treating disorders which are associated with aberrant expression or activity of h-ig6p, including pancreatic disorders. Examples of such disorders include diabetes (e.g., type 2 diabetes, maturity-onset diabetes of the young, and the like), hyperinsulinism, and glycogen storage diseases. Pharmaceutical compositions comprising a polypeptide of the invention, a nucleic acid molecule of the invention, a modulator of the invention, and combinations of these are included within the scope of the invention.

Other features and advantages of the invention will be apparent from the following detailed description and claims.

BRIEF DESCRIPTION OF THE DRAWINGS

FIG. 1 is the nucleotide sequence (SEQ ID NO: 1) of the cDNA described herein which encodes h-ig6p.

FIG. 2, comprising FIGS. 2A–2C, is the amino acid sequence (SEQ ID NO: 3) of h-ig6p.

FIG. 3, comprising FIGS. 3A and 3B, is an alignment (made using the ALIGN software {Myers and Miller (1989) CABIOS, ver. 2.0}; BLOSUM62 scoring matrix, gap penalties 12/4) of the amino acid sequence (SEQ ID NO: 3) of h-ig6p ("H") and the amino acid sequence (SEQ ID NO: 4) of the murine pancreatic islet-specific glucose-6-phosphatase described by Arden et al., (1999, Diabetes 48:531–542).

FIG. 6, comprising FIGS. 6A to 6C, is an alignment of the amino acid sequences of h-ig6p ("Hp"; SEQ ID NO: 3), murine pancreatic islet-specific glucose-6-phosphatase ("Mp"; SEQ ID NO: 4), cichlid fish liver glucose-6-phosphatase ("Fl"; SEQ ID NO: 24), murine liver glucose-6-phosphatase ("Ml"; SEQ ID NO: 25), canine liver glucose-6-phosphatase ("Cl"; SEQ ID NO: 26), and human liver glucose-6-phosphatase ("Hl"; SEQ ID NO: 27). Bold, underlined residues indicate predicted transmembrane regions, as indicated in Arden et al. (1999, Diabetes 48:531–542).

DETAILED DESCRIPTION

Figure 4:
FIG. 4 is an image that depicts expression of mRNA encoding h-ig6p in human pancreas tissue, particularly in pancreatic islet cells.
Figure 5:
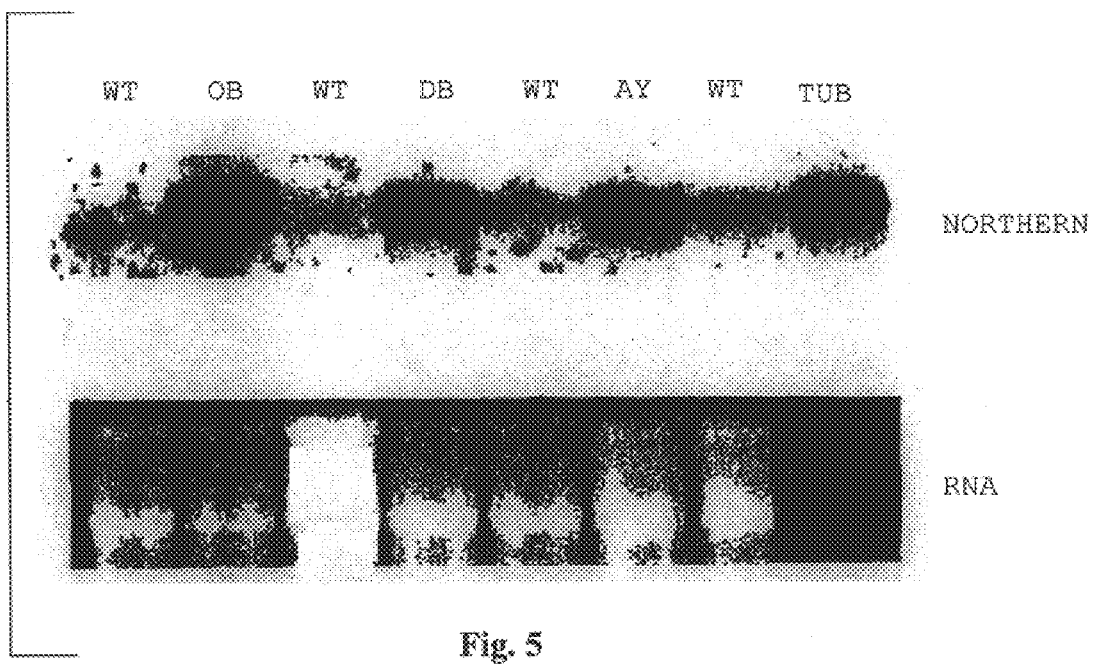
FIG. 5 is an image which depicts detection of RNA encoding h-ig6p in pancreatic tissue samples obtained from wild type ("WT") and obese/diabetic mouse strains ob ("OB"), db ("DB"), agouti ("AY"), and tubby ("TUB").

The present invention is based on the discovery of a cDNA molecule encoding the catalytic subunit of human pancreatic glucose-6-phosphatase (G6Pase) that is expressed specifically in islet of Langerhans cells. This subunit is herein designated h-ig6p.

A cDNA clone encoding h-ig6p was isolated from a human islet of Langerhans cell cDNA library. h-ig6p is predicted by structural analysis to be a transmembrane protein that can be localized at the endoplasmic reticulum. Cell fractionation experiments performed using Cos-7 cells which had been transformed with an expression vector encoding h-ig6p indicated that h-ig6p localizes to the microsomal fraction of fractionated cells, further indicating that h-ig6p associates with the endoplasmic reticulum under physiological conditions.

The full length of the cDNA encoding h-ig6p (FIG. 1; SEQ ID NO: 1) is 1138 nucleotide residues. The ORF of this cDNA, nucleotide residues 54 to 1121 of SEQ ID NO: 1 (i.e. SEQ ID NO: 2), encodes a 355-amino acid residue transmembrane protein (FIG. 2; SEQ ID NO: 3). A clone comprising a nucleic acid having a sequence comprising SEQ ID NO: 1 was deposited with the American Type Culture Collection® (ATCC®; 10801 University Blvd. Manassas, Va. 20110-2209) on Jul. 28, 2000, and was assigned accession number PTA-2282.

In addition to purified h-ig6p protein, the invention includes fragments, derivatives, and variants (e.g., allelic variants and highly homologous polypeptides) of h-ig6p protein, as described herein. These proteins, fragments, derivatives, and variants are collectively referred to herein as polypeptides of the invention or proteins of the invention. In addition to full-length h-ig6p (i.e., the protein having the amino acid sequence SEQ ID NO: 3), the invention includes portions of h-ig6p which have structural, functional, or catalytic significance, as described herein.

The invention also includes nucleic acid molecules which encode h-ig6p and fragments, derivatives, and variants thereof. Such nucleic acids include, for example, a DNA molecule having the nucleotide sequence listed in SEQ ID NO: 1 or some portion thereof, such as a portion encoding a domain of h-ig6p described herein, and a DNA molecule having the nucleotide sequence of the clone deposited with ATCC® on Jul. 28, 2000 as accession number PTA-2282. Nucleic acid molecules of the invention also include those which do not necessarily encode h-ig6p or a structurally-, functionally-, or catalytically-relevant portion thereof, but which hybridize with a nucleic acid which does encode such a portion (particularly including nucleic acid molecules which hybridize with such nucleic acids under stringent binding conditions). These nucleic acids are collectively referred to as nucleic acid molecules of the invention.

h-ig6p proteins typically comprise a variety of potential post-translational modification sites (often within an extra-cellular domain), such as those described herein in Table I, as predicted by computerized sequence analysis of h-ig6p using amino acid sequence comparison software (comparing the amino acid sequence of h-ig6p with the information in the PROSITE database {rel. 12.2; February, 1995} and the Hidden Markov Models database {Rel. PFAM 3.3}). In certain embodiments, a protein of the invention has at least 1, 2, 4, 6, 10, or all 16 of the post-translational modification sites listed in Table I.

TABLE I

| Type of Potential Modification Site or Domain | Amino Acid Residues of SEQ ID NO: 3 | Amino Acid Sequence |
| --- | --- | --- |
| N-glycosylation site | 50 to 53 | NQTV |
|  | 92 to 95 | NHSS |
|  | 287 to 290 | NYTL |
| Protein kinase C phosphorylation site | 281 to 283 | SCR |
|  | 291 to 293 | SFR |
|  | 350 to 352 | SGK |
| Casein kinase II phosphorylation site | 103 to 106 | TTCE |
|  | 314 to 317 | THEE |
| N-myristoylation site | 110 to 115 | GSPSGH |
|  | 182 to 187 | GVIGGM |
|  | 198 to 203 | GIQTAS |
|  | 258 to 263 | GLVRNL |
|  | 264 to 269 | GVLFGL |
|  | 285 to 290 | GNNYTL |
| Amidation site | 350 to 353 | SGKK |
| Endoplasmic reticulum membrane retention site | 351 to 355 | KKSQ | h-ig6p protein exhibits sequence similarity to a murine pancreatic islet-specific G6Pase catalytic subunit, as indicated herein in FIG. 3. FIG. 3 is an alignment of the amino acid sequences of h-ig6p (SEQ ID NO: 3) and the murine pancreatic islet-specific G6Pase catalytic subunit (SEQ ID NO: 23; GENBANK™ accession number Z47787; Arden et al., 1999, Diabetes 48:531–542; Ebert et al., 1999, Diabetes 48:543–554). In this alignment (made using the ALIGN software {Myers and Miller (1989) CABIOS, ver. 2.0}; BLOSUM62 scoring matrix, 10 gap penalties 12/4), the amino acid sequences of the proteins are 84.2% identical and 87.0% similar.

In an alignment of the nucleotide sequences of cDNA encoding human h-ig6p protein (SEQ ID NO: 1) and murine cDNA encoding pancreatic islet-specific G6Pase catalytic subunit (SEQ ID NO: 22; the alignment made using the ALIGN software {Myers and Miller (1989) CABIOS, ver. 2.0}; PAM120 scoring matrix, gap penalties 12/4), the nucleic acid sequences of the cDNAs are 90.0% identical. The sequence similarity between h-ig6p and murine pancreatic islet-specific G6Pase catalytic subunit and the cDNAs which encode them is an indication that these proteins have analogous, or overlapping, physiological roles. h-ig6p is likely the human ortholog of murine pancreatic islet-specific G6Pase catalytic subunit. The presence of an endoplasmic reticulum membrane retention site at the carboxyl terminus of h-ig6p is another indication that this protein is a catalytic subunit of pancreatic islet-specific G6Pase, having physiological function analogous to the murine islet-specific G6Pase catalytic subunit.

h-ig6p amino acid sequence also exhibits high homology with murine pancreatic islet G6Pase catalytic subunit amino acid sequence reported by Arden et al., within membrane-spanning regions, conservation of charged residues (e.g. residues 65, 72, 168, 191, 226, 261, 274, 293, 305, and 327 of each of SEQ ID NOs: 3 and 4) within those regions, and conservation of the putative N-glycosylation site at residue 92 of SEQ ID NOs: 3 and 4. These charged residues are also conserved among integral membrane proteins which facilitate transmembrane transport of phosphorylated glycolytic intermediates. Regions of h-ig6p (including the region spanning residues 59–66 and 68–80 of SEQ ID NO: 3, the region spanning residues 111–118 and 120–127 of SEQ ID NO: 3, and the region spanning residues 160–188 of SEQ ID NO: 3) are conserved among h-ig6p, murine pancreatic islet-specific G6Pase, liver G6Pases, bacterial vanadate-sensitive haloperoxidases, mammalian type 2 phosphatidic acid phosphatases, bacterial acid phosphatases, and the Drosophila developmental protein designated Wunen, indicating that these regions can be important to one or more of the structure, function, and catalytic activity of h-ig6p.

Conservation of amino acid residues at positions corresponding to residues in the catalytic sites of soluble haloperoxidases and phosphatases among those enzymes, murine pancreatic islet-specific G6Pase, and h-ig6p (i.e., at residues 72, 79, 80, 112–115, 167, 168, and 174 of SEQ ID NO: 3) is an indication that conservation of these residues can be important for maintaining one or more of the structure, function, and catalytic activity of a polypeptide of the invention.

Postulated catalytically-relevant residues identified in liver G6Pase are also conserved in murine pancreatic islet G6Pase catalytic subunit and in h-ig6p (e.g., residues 72, 80, 167, and 168 of SEQ ID NO: 3).

The transmembrane segment prediction program MEMSAT (Jones et al., 1994, Biochemistry. 33:3038–3049) was used to predict the location of likely transmembrane domains of h-ig6p. Transmembrane domains were identified at about residues 57–76, 116–138, 148–170, 177–193, 212–234, 256–273, 294–310, and 319–343 of SEQ ID NO: 3. By analogy with the topology predicted for the murine islet-specific G6Pase catalytic subunit, the transmembrane domain predicted at residues 212–234 of SEQ ID NO: 3 may instead be two distinct transmembrane domains, one at about residues 212–217 of SEQ ID NO: 3 and the other at about residues 221–234 of SEQ ID NO: 3. It is believed that h-ig6p is normally oriented in the membrane of the endoplasmic reticulum such that its amino terminus and the non-transmembrane segments which include residues 79, 80, 112–115, and 174 of SEQ ID NO: 3 are exposed on the lumenal side of the endoplasmic reticular membrane, and that the carboxyl terminus of the protein extends into the cytosol. This topology is consistent with the topology observed for another endoplasmic reticulum-associated G6Pase subunit (van de Werve et al., 2000, Eur. J. Biochem. 267:1533–1549). In another embodiment, h-ig6p is oriented in the membrane of the endoplasmic reticulum such that its amino terminus and the non-transmembrane segments which include residues 79, 80, 112–115, and 174 of SEQ ID NO: 3 are exposed on the cytosolic side of the endoplasmic reticular membrane, and that the carboxyl terminus of the protein extends into the lumen of the endoplasmic reticulum.

In yet another embodiment, h-ig6p can share the topology and orientation predicted in Arden et al. (1999, Diabetes 48:531–542) for the liver G6Pases of cichlid fish, mouse, dog, and human and for the murine pancreatic G6Pase. FIG. 6 depicts an alignment of the amino acid sequence of h-ig6p with the amino acid sequences of the aforementioned enzymes. In this embodiment residues 1 to about 27 of h-ig6p are on the non-cytoplasmic face of the membrane and, as shown in FIG. 6, transmembrane regions exist at about residues 28–47, 57–76, 116–136, 151–173, 179–193, 210–230, 256–278, 290–307, and 319–343 of SEQ ID NO: 3.

Northern blot experiments performed using standard methods demonstrated significant expression of mRNA encoding h-ig6p in human pancreas tissue and, to a lesser extent, in testis tissue, although the size of the mRNA detected in testis tissue differed from that detected in pancreas tissue.

Expression could not be detected in Northern blot experiments in heart, brain, placenta, lung, liver, muscle, kidney, spleen, thymus, prostate, ovary, small intestine, colon, stomach, thyroid, spinal cord, lymph node, trachea, adrenal gland, or bone marrow tissues.

In reverse-transcription PCR (RT-PCR) experiments performed using TAQMAN® reagents, expression of mRNA encoding h-ig6p was detected in pancreas tissue, but could not be detected at a significant level in, for example, normal artery, normal vein, aorta smooth muscle, coronary artery smooth muscle, umbilical vein epithelium (static or sheared), normal heart, congestive heart failure heart, kidney, skeletal muscle, normal adipose, primary osteoblast, differentiated osteoblast, normal skin, normal spinal cord, normal brain cortex, normal brain hypothalamus, nerve, dorsal root ganglion, glial cells (astrocytes), glioblastoma, normal breast, breast tumor, normal ovarian, ovarian tumor, normal prostate, prostate tumor, prostate epithelium, normal colon, colon tumor, irritable bowel disease colon, normal lung, lung tumor, chronic obstructive pulmonary disorder lung, normal liver, fibrosis liver, dermal cells (fibroblasts), normal spleen, normal tonsil, lymph node, small intestine, skin decubitus, synovium, bone marrow mononuclear, and activated peripheral blood mononuclear tissues under the conditions used.

In contrast, expression of mRNA encoding human liver G6Pase could be detected at the indicated relative levels in only the following tissues in RT-PCR experiments:

Normal liver: 43

Fibrosed liver: 23.77

Kidney: 25.47

Small intestine: 6.46.

Expression of mRNA encoding human liver G6Pase could not be detected at significant levels in RT-PCR experiments in normal artery, normal vein, aorta smooth muscle, coronary artery smooth muscle, umbilical vein epithelium (static or sheared), normal heart, congestive heart failure heart, skeletal muscle, normal adipose, pancreas, primary osteoblast, differentiated osteoblast, normal skin, normal spinal cord, normal brain cortex, normal brain hypothalamus, nerve, dorsal root ganglion, glial cells (astrocytes), glioblastoma, normal breast, breast tumor, normal ovarian, ovarian tumor, normal prostate, prostate tumor, prostate epithelium, normal colon, colon tumor, irritable bowel disease colon, normal lung, lung tumor, chronic obstructive pulmonary disorder lung, dermal cells (fibroblasts), normal spleen, normal tonsil, lymph node, skin decubitus, synovium, bone marrow mononuclear, and activated peripheral blood mononuclear tissues under the conditions used.

In situ hybridization experiments, performed using standard methods, demonstrated that h-ig6p is expressed in human pancreatic islet cells, as illustrated in FIG. 4. Expression of mRNA encoding murine islet-specific G6Pase was up-regulated (i.e., relative to wild type mice) in the ob, db, agouti, and tubby strains of mice. These strains are art-accepted mouse models of obesity, diabetes, or both. Overexpression of the murine islet-specific G6Pase was demonstrated to be correlated with the degree of hyperinsulinemia in the mouse models, indicating a correlation between h-ig6p overexpression and human hyperinsulinemia. This observation suggests that inhibition of h-ig6p expression (or inhibition of the activity of h-ig6p protein) can prevent or reverse abnormally low insulin secretion in humans, alleviating or preventing disorders associated with abnormally low insulin levels (e.g., diabetes). Conversely, this observation also suggests that enhancement of h-ig6p expression (or enhancement of the activity of h-ig6p protein) can prevent or reverse abnormally high insulin secretion in humans, alleviating or preventing disorders associated with abnormally high insulin levels.

The h-ig6p protein described herein can bind with one or more phosphorylated or non-phosphorylated carbohydrates (e.g. glucose) and can catalyze one or both of interconversion between the phosphorylated and non-phosphorylated forms of the carbohydrate (e.g., glucose$\leftrightarrow$G6P) and transmembrane transport of the phosphorylated or non-phosphorylated form of the carbohydrate. Homology of h-ig6p with liver and kidney G6Pases suggests that, like these enzymes, h-ig6p can participate in multimeric membrane-associated protein complexes including, for example, proteins which bind one or more of the phosphorylated or non-phosphorylated form of the carbohydrate, proteins which facilitate or catalyze transmembrane transport (i.e., across the cytoplasmic or endoplasmic reticular membrane) of one or more of the phosphorylated or non-phosphorylated form of the carbohydrate, enzymes which catalyze interconversion of the phosphorylated and non-phosphorylated forms of the carbohydrate, enzymes which catalyze glycolytic reactions, and enzymes which catalyze gluconeogenic reactions.

Because G6P (and xyulose-5-phosphate) mediate gene transcription induced by glucose or carbohydrate feeding (Massillon et al., 1998, J. Biol., Chem. 273:228–234), the ability of h-ig6p to modulate intracellular G6P levels indicates that h-ig6p can act as a regulator of gene transcription that is responsive to intracellular (e.g. cytosolic or endoplasmic reticular) glucose concentration. When h-ig6p is present, optionally in association with other proteins, in the cytoplasmic membrane of a pancreatic islet cell, it can also regulate gene expression within the cell in response to blood (or other extracellular) glucose concentration.

When h-ig6p is present, optionally in association with other proteins, in the membrane surrounding the endoplasmic reticulum in a cell, it can regulate one or both of expression of protein secreted into the endoplasmic reticulum and processing of protein (e.g., a hormone, a prohormone, or a pre-prohormone) present with the endoplasmic reticulum. Without being bound by any particular theory of operation, it is believed that h-ig6p can interact with one or more proteins (e.g., ribosomal proteins or prohormone processing enzymes) associated with expression, processing, or secretion of hormone polypeptides, and that the manner in which h-ig6p interacts with such proteins can be altered upon or following interaction of h-ig6p with G6P. Thus, h-ig6p can act as an intracellular 'sensor' of cellular G6P content, and can modulate (i.e., enhance or retard) hormone expression, processing, or secretion in response to the cellular G6P level.

For example, because h-ig6p can associate with the endoplasmic reticulum in pancreas alpha and beta cells, this protein can modulate expression of hormones (e.g., insulin and glucagon) which are transported into the endoplasmic reticulum of these cells, and post-translational processing (e.g., cleavage of pre-proinsulin to form proinsulin and cleavage of proinsulin to form insulin) of such hormones. Ability of h-ig6p to modulate production and activation of pancreatic hormones is an indication that h-ig6p proteins, nucleic acids, and modulators thereof can be used to prognosticate, diagnose, inhibit, prevent, or treat disorders with which aberrant function of these hormones is associated. Examples of these disorders include carbohydrate metabolism disorders (e.g., diabetes).

Because insulin and glucagon can modulate the metabolic rate of one or more tissues in a mammal (e.g., a human), expression of h-ig6p in cells which produce these hormones, and association of h-ig6p with the endoplasmic reticulum (within which these hormones are produced and processed) in these cells indicates that h-ig6p proteins, nucleic acids, and modulators thereof can be administered to pancreatic cells (or systemically) in order to modulate (i.e., increase or decrease) the rate of metabolism in other (i.e., non-pancreas) cells or tissues. For example, homology of h-ig6p with the murine G6Pase catalytic subunit (and presumably with the rat G6Pase catalytic subunit) indicates that overexpression of h-ig6p in pancreatic cells can uncouple glucose-stimulated insulin secretion, leading to increased hepatic glucose production and impaired glucose-stimulated insulin secretion. The ability of the polypeptides, nucleic acid molecules, and modulators of the invention to affect metabolic rate indicates that these agents can be used to control body weight in humans (i.e., to enhance or inhibit weight gain or to enhance or inhibit weight loss).

The activities which can be attributed to h-ig6p indicate that this protein modulates glucose-stimulated insulin secretion by pancreatic beta cells, and can also modulate glucose-regulated glucagon secretion by pancreatic alpha cells. Thus, agents including polypeptides, nucleic acid molecules, and modulators of the invention, can be used to prognosticate, prevent, diagnose, or treat one or more of disorders associated with aberrant insulin or glucagon secretion. Examples of such disorders include diabetes (including diabetes of various types, such as type 2 diabetes or maturity-onset diabetes of the young) and hyperinsulinism. The agents can also be used to prevent, alleviate, or eliminate symptoms associated with such disorders (e.g. hepatic glucose production or defects in insulin-dependent peripheral glucose utilization associated with type 2 diabetes, diabetic ketoacidosis, non-ketotic hyperglycemic-hyperosmolar coma, hyperglycemia, hypoglycemia, atherosclerosis, coronary artery disease, wasting disorders, diabetic retinopathy, and the like). Because insulin and glucagon are involved in regulating uptake and storage of glucose by the body, these agents can also be used to modulate body weight (i.e. maintenance of body weight or modulation of weight gain or loss) in humans.

Correlation in mouse models of obesity and diabetes of the obese or diabetic phenotype with overexpression of the gene encoding h-ig6p is an indication that enhancement of the activity or level of expression of h-ig6p inhibits insulin secretion by pancreatic islet beta cells and, conversely, that inhibition of h-ig6p activity or expression enhances insulin secretion by those cells. In addition, these data indicate that modulating expression or activity of h-ig6p can inhibit obesity and lead to weight gain and, conversely, that enhancing expression or activity of h-ig6p can enhance weight gain in a human. Thus, the results presented in this disclosure demonstrate that modulation of h-ig6p expression or activity can be useful for alleviation, inhibition, or prevention of various pancreatic disorders, including metabolic disorders (e.g., carbohydrate metabolism disorders such as diabetes, obesity, and hyperinsulinemia).

Localization of pancreatic islet G6Pase catalytic subunits, including h-ig6p, in the membrane of the endoplasmic reticulum indicates that these enzymes can have a physiological role in other processes which involve hydrolysis of phosphorylated carbohydrates. By way of example, these enzymes can modulate glycolysis of proteins (e.g. by trimming core-glycosylated proteins). These enzymes can also modulate accumulation of physiologically relevant ions (e.g. phosphate or calcium ions) within the endoplasmic reticulum (or another membrane-bound compartment, such as the cytosol or the nucleus) by mediating transport of a phosphorylated carbohydrate into or out of the compartment. Phosphohydrolysis of a phosphorylated carbohydrate within the compartment can increase the phosphate concentration within the compartment which, in turn, can be used to drive import from, export to, or exchange of another ion with the extra-compartmental milieu.

Various aspects of the invention are described in further detail in the following subsections.

I. Isolated Nucleic Acid Molecules

The invention includes a variety of isolated nucleic acid molecules including:

(i) isolated nucleic acid molecules which encode a polypeptide of the invention (e.g., an isolated nucleic acid molecule that encodes full length h-ig6p or a portion of h-ig6p that includes a structural, functional, or catalytic feature described herein);

(ii) isolated nucleic acid molecules which have a sequence that is sufficiently identical to, or sufficiently complementary to, all or part of SEQ ID NO: 1 that they can be used as hybridizable probes or as primers for amplification of a nucleic acid encoding all or a portion of h-ig6p;

(iii) isolated nucleic acid molecules which have a sequence that is sufficiently identical to, or sufficiently complementary to, all or part of SEQ ID NO: 1 that they can be used to inhibit expression of the gene encoding h-ig6p (i.e., either by inhibiting DNA transcription or RNA translation); and (iv) isolated nucleic acid molecules (e.g., ribozymes) which comprise a portion having a sequence that is sufficiently identical to, or sufficiently complementary to, all or part of SEQ ID NO: 1 that they hybridize with a substrate nucleic acid having the sequence SEQ ID NO: 1, and which further comprise a portion that catalyzes modification (e.g., cleavage) of the substrate nucleic acid.

Further details of these isolated nucleic acid molecules and how they can be made and used are described in the remainder of this subsection.

As used herein, the term "nucleic acid molecule" includes DNA molecules (e.g., cDNA or genomic DNA) and RNA molecules (e.g., mRNA) and analogs of the DNA or RNA generated using nucleotide analogs. The nucleic acid molecule can be single-stranded or double-stranded, and can also include those nucleic acid molecules which form triple helical structures. See generally Helene (1991) Anticancer Drug Des. 6(6):569–584; Helene (1992) Ann. N.Y. Acad. Sci. 660:27–36; and Maher (1992) Bioassays 14(12):807–815.

Nucleic acid molecules also include those which comprise one or more nucleotide residues having a modified purine or pyrimidine moiety, a modified sugar-phosphate backbone. Such modified base moieties and modified backbones are known in the art. Examples of modified base moieties include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (V), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (V), 5-methyl-2-thiouracil, 3-(3-amino-3-N-2-carboxypropyl) uracil, (acp3) W, and 2,6-diaminopurine. Examples of nucleic acid molecules which have modified sugar-phosphate backbones include peptide nucleic acids ("PNAs"; see Hyrup et al. (1996) Bioorganic & Medicinal Chemistry 4(1): 5–23; Perry-O'Keefe et al. (1996) Proc. Natl. Acad. Sci. USA 93: 14670–14675), and nucleic acids having one or more internucleoside linkages selected from the group consisting of phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate, phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), dimethylene-sulfoxide ($-CH_2-SO-CH_2-$), dimethylene-sulfone ($-CH_2-SO_2-CH_2-$), 2'-O-alkyl, 2'-deoxy2'-fluoro phosphorothioate, and sulfone linkages (see, e.g., Uhlmann et al., 1990, Chem. Rev. 90:543–584; Schneider et al., 1990, Tetrahedron Lett. 31:335).

An "isolated" nucleic acid molecule is one which is separated from other nucleic acid molecules which are present in the natural source of the nucleic acid molecule. Preferably, an "isolated" nucleic acid molecule is free of regions (preferably regions encoding protein) which naturally flank the nucleic acid (i.e., polynucleotides located at the 5' and 3' ends of the nucleic acid) in the genomic DNA of the organism from which the nucleic acid molecule is derived. For example, the invention includes isolated nucleic acid molecule which comprise one or two polynucleotide regions flanking the isolated nucleic acid molecule, wherein the flanking polynucleotides together comprise fewer than about 5000, 4000, 3000, 2000, 1000, 500, or 100 nucleotide residues.

The terms "nucleotides" and "nucleotide residues" are used interchangeably herein to refer to individual ribonucleotide or deoxyribonucleotide moieties of a polymeric nucleic acid. Thus, A, C, G, and T each represent an individual nucleotide residue of the nucleic acid having the sequence 5'-ACGT-3'.

The nucleotide sequences of the isolated nucleic acid molecules of the invention are based on the nucleotide sequence (SEQ ID NO: 1) of the cDNA described herein which encodes h-ig6p. A nucleic acid clone having a sequence comprising SEQ ID NO: 1 was deposited with ATCC® on Jul. 28, 2000 as accession number PTA-2282, and the nucleotide sequences of the isolated nucleic acid molecules of the invention can be based on the nucleotide sequence of this deposited clone as well.

The invention includes nucleic acid molecules which have a sequence which comprises, or consists of, all or a portion of SEQ ID NO: 1, the nucleotide sequence of the clone deposited with ATCC® on Jul. 28, 2000 as accession number PTA-2282, or the complement thereof. The portion can comprise 20, 25, 30, 35, 40, 50, 75, 100, 150, 200, 350, 500, 750, 1000, 1138, or any intermediate number of consecutive residues of SEQ ID NO: 1, the nucleotide sequence of the clone deposited with ATCC® on Jul. 28, 2000 as accession number PTA-2282, or the complement thereof. Alternatively, the isolated nucleic acid molecule can comprise, or consist of, a nucleic acid having a sequence that is at least 91% (or 92%, 95%, 98%, or 99% or more) identical to all or a portion (e.g., 20, 25, 30, 35, 40, 50, 75, 100, 150, 200, 350, 500, 750, 1000, 1138, or any intermediate number of consecutive residues) of SEQ ID NO: 1, of the nucleotide sequence of the clone deposited with ATCC® on Jul. 28, 2000 as accession number PTA-2282, or of the complement thereof.

The nucleic acid molecule having the sequence SEQ ID NO: 1 (and the clone deposited with ATCC® on Jul. 28, 2000 as accession number PTA-2282) encode h-ig6p protein, which has the amino acid sequence SEQ ID NO: 3. The isolated nucleic acid molecules of the invention include nucleic acid molecules which do not have the sequence SEQ ID NO: 1, but nonetheless encode a protein having the amino acid sequence SEQ ID NO: 3 or a protein having an amino acid sequence that is at least 85% (or 90%, 95%, 98%, or 99% or more) identical to all or a portion of SEQ ID NO: 3. Such nucleic acid molecules include those which encode all or a portion of SEQ ID NO: 3 and which have a nucleotide sequence that differs from the corresponding portion of SEQ ID NO: 1 owing to the degeneracy of the genetic code (i.e., the nucleotide sequence includes at least one codon synonymous with, but not identical to, the corresponding codon of SEQ ID NO: 1). When the amino acid sequence encoded by the nucleic acid molecule differs from the corresponding portion of SEQ ID NO: 3, it is preferred that the amino acid sequence not differ at residues described herein as having structural, functional, or catalytic significance.

Isolated nucleic acid molecules which encode h-ig6p having one or more amino acid substitutions, insertions, or deletions at selected positions can be made using known methods (e.g., site-directed mutagenesis or PCR-mediated mutagenesis). Amino acid residue substitutions are preferably not made at residues with structural, functional, or catalytic significance, and insertions and deletions are preferably not made within structural, functional, or catalytic domains identified herein. Alternatively, mutations can be introduced randomly along all or part of the coding sequence, such as by saturation mutagenesis, and the resulting mutants can be screened for biological activity in order to identify mutants that retain functional or catalytic activity of h-ig6p.

Other isolated nucleic acid molecules of the invention encode allelic variants of h-ig6p (i.e., including both allelic variants wherein both the amino acid sequence and the nucleotide sequence corresponding to h-ig6p differ from SEQ ID NOs: 3 and 1 and allelic variants wherein h-ig6p has the amino acid sequence SEQ ID NO: 3, but wherein the nucleotide sequence that encodes this protein differs from SEQ ID NO: 1). These allelic variants include those commonly referred to as polymorphisms, including single nucleotide polymorphisms (i.e., allelic variants wherein the nucleotide sequence encoding h-ig6p differs from SEQ ID NO: 1 only at one or more non-adjacent nucleotide residues). Typically, allelic variants are encoded by the same genetic locus among different individuals in a species of organism.

The degree of sequence identity between two nucleic acid sequences can be assessed by aligning the sequences and comparing the number of identical residues to the number of total residues in the overlapping region (i.e., making no allowance for insertions and deletions). Alternatively, and preferably, the degree of sequence identity can be assessed using an algorithm that accounts for the possibility of inserted and deleted residues. An example of such an algorithm is that incorporated into the NBLAST computer program (see Karlin et al., 1990, Proc. Natl. Acad. Sci. USA 87:2264–2268; Karlin et al., 1993, Proc. Natl. Acad. Sci. USA 90:5873–5877; Altschul et al., 1990, J. Mol. Biol. 215:403–410; Altschul et al., 1997, Nucl. Acids Res. 25:3389–3402; States et al., 1991, Methods 3:66–70), which can be obtained, for example at the World Wide Web site having the universal resource locator http://www.ncbi.nlm.nih.gov. Preferred parameters used in the NBLAST program are wordlength=12, PAM120 weight residue table, gap existence penalty=12, gap length penalty=4 per residue, expectation value=10.0, mismatch penalty=−3, and match reward=1.

The degree of sequence homology between two nucleic acid molecules can also be assessed by determining the ability of the molecules to hybridize with one another. Nucleic acid molecules of the invention include those which hybridize under stringent conditions with a nucleic acid having a sequence comprising SEQ ID NO: 1, with the clone deposited with ATCC® on Jul. 28, 2000 as accession number PTA-2282, or with the complement thereof. An example of stringent hybridization conditions is hybridization in 6×sodium chloride/sodium citrate buffer at pH 7.4 (SSC) at about 45° C., followed by one or more washes in 0.2×SSC, 0.1% SDS at 65° C.

Isolated nucleic acid molecules which encode full length h-ig6p or a biologically active portion thereof (i.e., a portion of h-ig6p that includes a structural, functional, or catalytic feature described herein) can be isolated or synthesized using standard molecular biology techniques, in view of the sequence information provided herein. For example, using a nucleic acid probe having a sequence comprising about 20–500 nucleotide residues of SEQ ID NO: 1, the nucleotide sequence of the clone deposited with ATCC® on Jul. 28, 2000 as accession number PTA-2282, or the complement thereof, nucleic acid molecules of the invention can be isolated from, for example, human tissue samples (e.g., as described in Sambrook et al., eds., Molecular Cloning: A Laboratory Manual, 2 nd ed., Cold Spring Harbor Laboratory, Cold Spring Harbor Laboratory Press, Cold Spring Harbor, N.Y., 1989). Alternatively, such nucleic acid molecules can be prepared by standard synthetic techniques (e.g., using an automated DNA synthesizer).

Nucleic acid molecules which encode a polypeptide of the invention can be used to express that polypeptide, either in vitro or in vivo, using methods known in the art. Briefly, the portion of the nucleic acid molecule which encodes the polypeptide must be operably linked with the control/regulatory sequences necessary for translation and, if necessary (i.e., if the nucleic acid molecule is DNA), transcription of the nucleic acid molecule. Such control/regulatory sequences are known in the art and include, for example, promoter sequences, ribosome binding sites, and the like. It is not necessary that the control/regulatory sequences of the gene encoding h-ig6p be used. Substantially any control/regulatory sequences that can be operably linked with the coding region of the nucleic acid molecule of the invention can be used. By way of example, control/regulatory sequences that render expression of h-ig6p inducible or tissue-specific are known and can be used.

Uses of oligonucleotides as probes for detecting or as primers for amplifying nucleic acids with which they hybridize are known in the art. Accordingly, nucleic acid molecules of the invention can be used as probes for detecting a nucleic acid encoding all or a portion of h-ig6p or for amplifying such a nucleic acid. Such probes can be isolated from naturally-occurring nucleic acids or synthesized, as described above. When used as probes or primers, the nucleic acid molecules of the invention preferably have a length of at least 20, 25, 30, 35, 40, 50, or more nucleic acid residues, and a sequence that is at least 91% (or 92%, 95%, 98%, or 99% or more) identical to the corresponding portion of SEQ ID NO: 1, the nucleotide sequence of the clone deposited with ATCC® on Jul. 28, 2000 as accession number PTA-2282, or the complement thereof, or at least being more identical to one of these human sequences than to an analogous portion of SEQ ID NO: 22. Such probes and primers can, optionally, have other moieties bound therewith, such as a detectable label (e.g., a radionuclide or an enzyme which catalyzes a chromogenic reaction), a relatively fixed substrate (e.g., a nylon membrane), or another polynucleotide (e.g., a portion of a plasmid or virus vector, or a polynucleotide adapted for insertion into a multiple restriction site of a vector). These probes and primers can be used as part of a diagnostic test kit for identifying cells or tissues which express h-ig6p (i.e., normally or aberrantly), or for assessing levels of h-ig6p expression.

The invention includes antisense nucleic acid molecules, i.e., molecules which are complementary to a nucleic acid molecule encoding a polypeptide of the invention (e.g., nucleic acid molecules which are complementary to at least a portion of the coding strand of a double-stranded cDNA molecule or complementary to at least a portion of an mRNA sequence encoding a polypeptide of the invention). Accordingly, an antisense nucleic acid can hybridize with a nucleic acid which encodes all or a portion of h-ig6p. Alternatively, an antisense nucleic acid molecule of the invention can be antisense with respect to all or part of a non-coding region of a nucleic acid encoding a polypeptide of the invention. The non-coding regions (e.g., 5' and 3' un-translated regions) include the 5' and 3' sequences which flank the coding region, and are not translated into amino acids. Antisense nucleic acid molecules can be, for example, about 5, 10, 15, 20, 25, 30, 35, 40, 45 or 50 nucleotides in length, and preferably have a sequence that is 91% (or 92%, 95%, 98%, or 99% or more) identical to a portion of SEQ ID NO: 1, to a portion of the nucleotide sequence of the clone deposited with ATCC® on Jul. 28, 2000 as accession number PTA-2282, or to the complement thereof.

The antisense nucleic acid molecules of the invention can be administered to a subject (or generated in situ, e.g., by transcribing a DNA) so that the antisense molecule hybridizes with or binds with cellular mRNA and/or genomic DNA encoding h-ig6p to thereby inhibit expression (i.e., by inhibiting transcription and/or translation). Inhibition in a cell of expression of a gene encoding h-ig6p (e.g., by inhibiting transcription of the gene or translation of the corresponding mRNA) inhibits h-ig6p activity in the cell, leading, for example, to enhanced insulin secretion (e.g., if the cell is a pancreatic islet beta cell). Furthermore, inhibition of h-ig6p activity in a cell can modulate (i.e., activate or inhibit) the cell's transmembrane signaling systems for detecting extracellular glucose levels. For example, the antisense nucleic acid molecule can be directly injected at a tissue site or modified to target selected cells following systemic administration (e.g., by modifying the antisense molecule {e.g., by attaching it to an antibody} so that it specifically binds with a receptor or antigen expressed on a selected cell surface). Any of the modifications of antisense molecules that are known in the art can be used to make antisense nucleic acid molecules of the invention (see, e.g., Gaultier et al. (1987) Nucleic Acids Res. 15:6625–6641; Inoue et al. (1987) Nucleic Acids Res. 15:6131–6148; Inoue et al. (1987) FEBS Lett. 215:327–330).

The invention also includes nucleic acid molecules (e.g., ribozymes) which have a portion which hybridizes with all or a portion of a substrate nucleic acid having the sequence of SEQ ID NO: 1, of the nucleotide sequence of the clone deposited with ATCC® on Jul. 28, 2000 as accession number PTA-2282, or of the complement thereof and a second portion which modifies (e.g., cleaves) the substrate nucleic acid. Ribozymes, for example, are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach (1988) Nature 334:585–591) can be used to catalytically cleave mRNA transcripts encoding h-ig6p to thereby translation thereof. A ribozyme having specificity for a nucleic acid molecule encoding h-ig6p (or another polypeptide of the invention) can be designed, based on the nucleotide sequences disclosed herein. For example, a derivative of a Tetrahymena L-19 IVS RNA can be constructed in which the nucleotide sequence of the active site is complementary to the nucleotide sequence to be cleaved, as described in Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) Science 261:1411–1418. Expression of such a ribozyme in a cell which expresses h-ig6p can inhibit expression of h-ig6p in the cell, leading to a decrease in the enzymatic activity of h-ig6p in the cell. As a result, insulin secretion can be enhanced, the sensitivity of the cell's signaling mechanism(s) for systemic glucose can be decreased, or some combination of the effects can occur.

Nucleic acid molecules of the invention can comprise appended groups such as peptides (e.g., antibodies or other specifically-binding proteins for targeting host cell receptors in vivo) or agents for facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the nucleic acid molecules of the invention can be conjugated with another molecule, e.g., a peptide, hybridization triggered cross-linking agent, transport agent, hybridization-triggered cleavage agent, etc., using methods known in the art.

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques. Proteins isolated from microsomal preparations of cells transfected with an expression vector encoding h-ig6p exhibited catalytic reactions that are characteristic of G6Pases (e.g., conversion of G6P to glucose), confirming that the isolated proteins are, in fact, a pancreas-specific form of G6Pase.

Biologically active portions of h-ig6p are able to catalyze conversion of glucose-6-phosphate to glucose in vitro, in vivo, or both. Biologically active portions preferably include the residues conserved among G6Pases, as noted above.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence of SEQ ID NO: 3, or the amino acid sequence encoded by the clone deposited with ATCC® on Jul. 28, 2000 as accession number PTA-2282, or of 15 or more {e.g., 30, 56, 57, 58, 60, 70, 80, 90, 100, 120, 140, 160, 180, 200, 250, 300, 350, or 355} consecutive residues thereof), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO: 3, or the amino acid sequence encoded by the clone deposited with ATCC® on Jul. 28, 2000 as accession number PTA-2282, or of 15 or more {e.g., 30, 56, 57, 58, 60, 70, 80, 90, 100, 120, 140, 160, 180, 200, 250, 300, 350, or 355} consecutive residues thereof. Other useful proteins are substantially identical (e.g., at least about 85%, 90%, 95%, 98%, or 99% or more) to SEQ ID NO: 3, or the amino acid sequence encoded by the clone deposited with ATCC® on Jul. 28, 2000 as accession number PTA-2282, or of 15 or more {e.g., 30, 56, 57, 58, 60, 70, 80, 90, 100, 120, 140, 160, 180, 200, 250, 300, 350, or 355} consecutive residues thereof and retain the functional activity of the protein of the corresponding naturally-occurring protein yet differ in amino acid sequence due to natural allelic variation or mutagenesis.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In a preferred embodiment, a mutant polypeptide that is a variant of a polypeptide of the invention can be assayed for: (1) the ability to form protein:protein interactions with proteins in a signaling pathway of the polypeptide of the invention; (2) the ability to bind a ligand of the polypeptide of the invention; or (3) the ability to bind to an intracellular target protein of the polypeptide of the invention. In yet another preferred embodiment, the mutant polypeptide can be assayed for the ability to modulate cellular proliferation, cellular migration or chemotaxis, or cellular differentiation.

To determine the percent identity of two amino acid sequences, the sequences are aligned for optimal comparison purposes (e.g., gaps can be introduced in the sequence of a first amino acid for optimal alignment with a second amino). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm used for the comparison of two amino acid sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the XBLAST programs of Altschul, et al. (1990) J. Mol. Biol. 215:403–410. BLAST amino acid sequence identity assessments can be performed using the XBLAST program, score=50, wordlength=3, BLOSUM62 scoring matrix, gap existence penalty =12, gap extension penalty=4 per residue, expectance=10.0, mismatch penalty=−3, reward for match= 1, to identify identity of amino acid sequences. To obtain gapped alignments for comparison purposes, Gapped BLAST can be used as described in Altschul et al. (1997) Nucleic Acids Res. 25:3389–3402. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, a signal sequence from another protein can be fused at the N-terminus of a polypeptide of the invention. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands. For example, antibodies described herein can be used to inhibit association between h-ig6p and an extracellular ligand thereof (e.g., glucose) if the antibody is contacted with the non-cytoplasmic face of h-ig6p. An intracellularly-expressed antibody can be used to inhibit association between h-ig6p and either an intracellular small molecular ligand (e.g., glucose-6-phosphate) or a cellular protein with which h-ig6p normally associates. Thus, either extracellular or intracellular antibodies can be used to inhibit an activity catalyzed or mediated by h-ig6p, and such antibodies can also be used to inhibit interactions between h-ig6p and other proteins.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, re-naturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811–7815; Delgrave et al. (1993) Protein Engineering 6(3):327–331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO: 3, or the amino acid sequence encoded by the clone deposited with ATCC® on Jul. 28, 2000 as accession number PTA-2282, and encompasses an epitope of the protein such that an antibody raised against the peptide forms a specific immune complex with the protein.

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention (e.g., an epitope of a polypeptide of the invention). A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77–96) or trioma techniques. The technology for producing hybridomas is well known (see generally Current Protocols in Immunology (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SURFZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine monoclonal antibody and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) Bio/Techniques 4:214; U.S. Pat. No. 5,225,539; Jones et al.

(1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rear-range during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al. (1994) Bio/technology 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibody substances of the invention can be used for modifying a given biological response, and the drug moiety conjugated with the antibody substance is not limited to classical chemical therapeutic agents. For example, the drug moiety can be a protein or polypeptide possessing a desired biological activity. Such proteins can include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2 nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982).

Alternatively, an antibody can be conjugated to a second antibody to form an antibody heteroconjugate as described by Segal in U.S. Pat. No. 4,676,980.

Accordingly, in one aspect, the invention provides substantially purified antibodies or fragment thereof, and non-human antibodies or fragments thereof, which antibodies or fragments specifically bind with (i) a polypeptide having the amino acid sequence of SEQ ID NO: 3 or the amino acid sequence encoded by the clone deposited with ATCC® on Jul. 28, 2000 as accession number PTA-2282;

(ii) a polypeptide fragment having the amino acid sequence of at least 15 (e.g., 30, 56, 57, 58, 60, 70, 80, 90, 100, 120, 140, 160, 180, 200, 250, 300, 350, or 355) consecutive amino acid residues of SEQ ID NO: 3 or the amino acid sequence encoded by the clone deposited with ATCC® on Jul. 28, 2000 as accession number PTA-2282;

(iii) a polypeptide having an amino acid sequence which is at least 95% identical to the amino acid sequence of SEQ ID NO: 3, or the amino acid sequence encoded by the clone deposited with ATCC® on Jul. 28, 2000 as accession number PTA-2282, or of 15 or more (e.g., 30, 56, 57, 58, 60, 70, 80, 90, 100, 120, 140, 160, 180, 200, 250, 300, 350, or 355) consecutive residues thereof, wherein the percent identity is determined using the ALIGN program of the GCG software package with a PAM120 weight residue table, a gap length penalty of 12, and a gap penalty of 4; or (iv) a polypeptide encoded by a nucleic acid molecule which hybridizes with a nucleic acid molecule having a nucleotide sequence complementary to SEQ ID NO: 1 or 2, or the nucleotide sequence of the clone deposited with ATCC® on Jul. 28, 2000 as accession number PTA-2282, under conditions of hybridization of 6×SSC at 45° C. and washing in 0.2×SSC, 0.1% SDS at 65° C.

In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind with:

(i) a polypeptide having the amino acid sequence of SEQ ID NO: 3 or the amino acid sequence encoded by the clone deposited with ATCC® on Jul. 28, 2000 as accession number PTA-2282;

(ii) a polypeptide fragment having the amino acid sequence of at least 15 (e.g., 30, 56, 57, 58, 60, 70, 80, 90, 100, 120, 140, 160, 180, 200, 250, 300, 350, or 355) consecutive amino acid residues of SEQ ID NO: 3 or the amino acid sequence encoded by the clone deposited with ATCC® on Jul. 28, 2000 as accession number PTA-2282;

(iii) a polypeptide having an amino acid sequence which is at least 95% identical to the amino acid sequence of SEQ ID NO: 3, or the amino acid sequence encoded by the clone deposited with ATCC® on Jul. 28, 2000 as accession number PTA-2282, or of 15 or more (e.g., 30, 56, 57, 58, 60, 70, 80, 90, 100, 120, 140, 160, 180, 200, 250, 300, 350, or 355) consecutive residues thereof, wherein the percent identity is determined using the ALIGN program of the GCG software package with a PAM120 weight residue table, a gap length penalty of 12, and a gap penalty of 4; or (iv) a polypeptide encoded by a nucleic acid molecule which hybridizes with a nucleic acid molecule having a nucleotide sequence complementary to SEQ ID NO: 1 or 2, or the nucleotide sequence of the clone deposited with ATCC® on Jul. 28, 2000 as accession number PTA-2282, under conditions of hybridization of 6×SSC at 45° C. and washing in 0.2×SSC, 0.1% SDS at 65° C.

Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind with:

(i) a polypeptide having the amino acid sequence of SEQ ID NO: 3 or the amino acid sequence encoded by the clone deposited with ATCC® on Jul. 28, 2000 as accession number PTA-2282;

(ii) a polypeptide fragment having the amino acid sequence of at least 15 (e.g., 30, 56, 57, 58, 60, 70, 80, 90, 100, 120, 140, 160, 180, 200, 250, 300, 350, or 355) consecutive amino acid residues of SEQ ID NO: 3 or the amino acid sequence encoded by the clone deposited with ATCC® on Jul. 28, 2000 as accession number PTA-2282;

(iii) a polypeptide having an amino acid sequence which is at least 95% identical to the amino acid sequence of SEQ ID NO: 3, or the amino acid sequence encoded by the clone deposited with ATCC® on Jul. 28, 2000 as accession number PTA-2282, or of 15 or more (e.g., 30, 56, 57, 58, 60, 70, 80, 90, 100, 120, 140, 160, 180, 200, 250, 300, 350, or 355) consecutive residues thereof, wherein the percent identity is determined using the ALIGN program of the GCG software package with a PAM120 weight residue table, a gap length penalty of 12, and a gap penalty of 4; or (iv) a polypeptide encoded by a nucleic acid molecule which hybridizes with a nucleic acid molecule having a nucleotide sequence complementary to SEQ ID NO: 1 or 2, or the nucleotide sequence of the clone deposited with ATCC® on Jul. 28, 2000 as accession number PTA-2282, under conditions of hybridization of 6×SSC at 45° C. and washing in 0.2×SSC, 0.1% SDS at 65° C.

The monoclonal antibodies can be human, humanized, chimeric and/or non-human antibodies.

Any of the antibodies of the invention can be conjugated with a therapeutic moiety or to a detectable substance. Non-limiting examples of detectable substances that can be conjugated with the antibodies of the invention are an enzyme, a prosthetic group, a fluorescent material, a luminescent material, a bioluminescent material, and a radioactive material.

The invention also provides a kit containing an antibody of the invention conjugated with a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes h-ig6p, the method comprising immunizing a mammal with a polypeptide of the invention. The polypeptide used as an immunogen comprises an amino acid sequence selected from the group consisting of:

(i) a polypeptide having the amino acid sequence of SEQ ID NO: 3 or the amino acid sequence encoded by the clone deposited with ATCC® on Jul. 28, 2000 as accession number PTA-2282;

(ii) a polypeptide fragment having the amino acid sequence of at least 15 (e.g., 30, 56, 57, 58, 60, 70, 80, 90, 100, 120, 140, 160, 180, 200, 250, 300, 350, or 355) consecutive amino acid residues of SEQ ID NO: 3 or the amino acid sequence encoded by the clone deposited with ATCC® on Jul. 28, 2000 as accession number PTA-2282;

(iii) a polypeptide having an amino acid sequence which is at least 95% identical to the amino acid sequence of SEQ ID NO: 3, or the amino acid sequence encoded by the clone deposited with ATCC® on Jul. 28, 2000 as accession number PTA-2282, or of 15 or more (e.g., 30, 56, 57, 58, 60, 70, 80, 90, 100, 120, 140, 160, 180, 200, 250, 300, 350, or 355) consecutive residues thereof, wherein the percent identity is determined using the ALIGN program of the GCG software package with a PAM120 weight residue table, a gap length penalty of 12, and a gap penalty of 4; or (iv) a polypeptide encoded by a nucleic acid molecule which hybridizes with a nucleic acid molecule having a nucleotide sequence complementary to SEQ ID NO: 1 or 2, or the nucleotide sequence of the clone deposited with ATCC® on Jul. 28, 2000 as accession number PTA-2282, under conditions of hybridization of 6×SSC at 45° C. and washing in 0.2×SSC, 0.1% SDS at 65° C.

After immunization, a sample is collected from the mammal that contains an antibody that specifically recognizes h-ig6p. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology, vol. 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., E. coli) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301–315) and pET 11d (Studier et al., Gene Expression Technology: Methods in Enzymology, vol. 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident lambda prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, Gene Expression Technology: Methods in Enzymology, vol. 185, Academic Press, San Diego, Calif. (1990) 119–128). Another strategy is to alter the nucleic acid sequence of the nucleic acid to be inserted into an expression vector so that the individual codons for each amino acid are those preferentially used in E. coli (Wada et al. (1992)

Nucleic Acids Res. 20:2111–2118). Such alteration of nucleic acid sequences of the invention can be carried out by standard DNA synthesis techniques.

In another embodiment, the expression vector is a yeast expression vector. Examples of vectors for expression in yeast S. cerevisiae include pYepSecl (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

Expression of h-ig6p in mammalian cells (e.g., pancreatic cells, including alpha and beta cells of pancreatic islets) can affect metabolic disorders, including various pancreatic disorders. For example, expression of h-ig6p in mammalian cells can affect carbohydrate metabolism in the cells. Expression of h-ig6p in pancreatic cells (e.g., pancreatic islet beta cells) can inhibit secretion of insulin. Furthermore, expression of h-ig6p in pancreatic cells (e.g., pancreatic islet alpha cells) can enhance glucagon secretion. Because h-ig6p can be involved in modulating intracellular levels of small molecules (e.g., glucose and G6P) that are involved in transmembrane signaling of extracellular and intracellular glucose, expression of h-ig6p in cells can affect the sensitivity of the signaling apparatus. The role of h-ig6p in intracellular G6P-mediated signaling indicates that expression of this protein from an expression vector can also influence intracellular G6P-mediated signaling. These properties of h-ig6p make expression vectors which encode this protein useful for treatment of pancreatic and metabolic disorders, such as carbohydrate metabolism disorders including diabetes, hyperinsulinemia, and obesity. Even in the absence of a disease state, such vectors can be used to affect carbohydrate metabolism and weight gain in humans.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the alpha-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous (e.g., h-ig6p) nucleic acid within a cell, cell line or microorganism can be modified by inserting a DNA regulatory element heterologous to the endogenous gene of interest into the genome of a cell, stable cell line or cloned microorganism such that the inserted regulatory element is operatively linked with the endogenous gene and controls, modulates or activates the endogenous gene. For example, endogenous h-ig6p which is normally "transcriptionally silent" or is expressed only at very low levels in a cell line or microorganism, can be activated by inserting a regulatory element which is capable of promoting the expression of a normally expressed gene product in that cell line or microorganism. Alternatively, transcriptionally silent, endogenous h-ig6p genes can be activated by insertion of a promiscuous regulatory element that works across cell types.

A heterologous regulatory element can be inserted into a stable cell line or cloned microorganism, such that it is operatively linked with and activates expression of endogenous h-ig6p genes, using techniques, such as targeted homologous recombination, which are well known to those of skill in the art, and described e.g., in Chappel, U.S. Pat. No. 5,272,071; PCT publication No. WO 91/06667, published May 16, 1991.

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell. Such host cells can be used, for example, in screening assays described herein.

By way of example, the host cell can be a cos-7 cell. Of course, numerous other mammalian cell lines (e.g., CHO cell line) can be used as host cells, depending on the particular characteristics desired, as is understood by the skilled artisan. In experiments described herein, cos-7 cells were transfected with no DNA (a control), with 10 micrograms of pcDNA3.1 (vector control), with 10 micrograms of human liver G6Pase-pcDNA3.1 (vector for expressing liver G6Pase), or with 10 micrograms of h-ig6p-pcDNA3.1 (vector for expressing h-ig6p). The cells were co-transfected with 2 micrograms of pCMV-beta-galactosidase vector so that expression of beta-galactosidase could be used to confirm transfection efficiency. Transfected cells were harvested about a day later, using a non-enzymatic harvesting method. The harvested cells were suspended in homogenization buffer (0.3 molar sucrose, 10 millimolar potassium MES buffer, pH adjusted to 6.5, 2 millimolar EGTA, and 1 millimolar $MgSO_4$) and homogenized on use using a POLY-TRAN™ homogenizer. The homogenate was centrifuged at 2000×g for 3 minutes, and then at 6000×g for 3 minutes. The supernatant was collected and centrifuged at 234,000×g for 1 hour. The microsomal fraction was re-suspended in 200 to 300 microliters of homogenization buffer to yield microsomal samples.

The host cells of the invention can also be used to produce non-human transgenic animals. For example, in one embodiment, a host cell of the invention is a fertilized oocyte or an embryonic stem cell into which a sequences encoding a polypeptide of the invention have been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986) and Wakayama et al., (1999), Proc. Natl. Acad. Sci. USA, 96:14984–14989. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CREMOPHOR™ EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody)

in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™, or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 to 100 milligram per kilogram body weight (generally 10 to 20 milligram per kilogram body weight). If the antibody is to act in the brain, a dosage of 50 to 100 milligram per kilogram body weight is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). For example, polypeptides of the invention can to used to (i) modulate cellular proliferation; (ii) modulate cellular differentiation; and/or (iii) modulate cellular adhesion. The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the jaw invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention. By way of example, these assays include assays for identifying compounds which enhance expression of h-ig6p, compounds which inhibit its expression, and compounds which act as agonists or antagonists of h-ig6p enzymatic activity. The assays can also be used to identify compounds which inhibit or enhance interaction of h-ig6p with one or more normal cellular proteins. As such, these screening assays can be used to identify compounds that are useful for alleviation, inhibition, or prevention of carbohydrate metabolism disorders described herein, such as diabetes and obesity. Compounds which enhance h-ig6p activity or expression can, for example, be used to alleviate or inhibit conditions (e.g., hyperinsulinemia or aberrant weight loss) associated with aberrantly high insulin secretion. Compounds which inhibit h-ig6p activity or expression can be used to alleviate or inhibit conditions (e.g., diabetes or obesity) associated with aberrantly low insulin secretion.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds can be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869) or phage (Scott and Smith (1990) Science 249:386–390; Devlin (1990) Science 249:404–406; Cwirla et al. (1990) Proc. Natl. Acad. Sci. USA 87:6378–6382; and Felici (1991) J. Mol. Biol. 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radio emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

Substantially any known or hereafter-developed method of assaying G6Pase activity can be used to assess the effect of a test compound on h-ig6p activity (including whether, or to what degree, h-ig6p is expressed). The activity can be assessed, for example, according to the methods disclosed in Arden et al., 1999, Diabetes 48:531–542). Colorimetric, radiometric, and other detection technologies can be used in the assay.

By way of example, G6Pase activities were assayed in microsomal samples in experiments described herein by incubating 20 microliters of a microsomal sample for 30 minutes at 30° C. with 40 microliters of assay buffer (100 millimolar dimethylglutarate, 20 millimolar sodium tartrate, 10 millimolar EDTA, and 20–40 millimolar glucose-6-phosphate, pH adjusted to 6.5). The reaction was terminated by adding 40 microliters of 10% (W/V) trichloroacetic acid to the assay mixture, and then the assay mixture was centrifuged for 5 minutes at 2000×g. 25 Microliters of the supernatant was transferred to a well on a 96-well plate, and 250 microliters of color reagent (1 part 4.2% (W/V) ammonium molybdate in 4 molar HCl, mixed with 3 parts 0.2% (W/V) malachite green, and then filtered after 30 minutes) was added to the well. The optical density at 650 nanometers (using sodium phosphate buffer as a standard) was measured in order to detect the reaction product. The concentration of protein in microsomal samples was determined using the Pierce Chemical Co. BCA™ bicinchoninic acid reagent. These assays demonstrated that the h-ig6p protein obtained from mammalian cell microsomal fractions described herein exhibits activity that is characteristic of a G6Pase enzyme.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention binds or interacts with in nature, for example, a molecule on the surface of a cell which expresses the selected protein, a molecule on the surface of a second cell, a molecule in the extracellular milieu, or a molecule associated with the internal surface of a cell membrane or a cytoplasmic molecule). A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., G6P, intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as described herein.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it can be desirable to use a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-{(3-cholamidopropyl)dimethylamminio}-1-propane sulfonate (CHAPS), 3-{(3-cholamidopropyl) dimethylamminio}-2-hydroxy-1-propane sulfonate (CHAPSO), or N-dodecyl-N,N-dimethyl-3 -ammonio-1 -propane sulfonate.

In more than one embodiment of the above assay methods of the present invention, it can be desirable to immobilize either the polypeptide of the invention or its target molecule to facilitate separation of complexed from non-complexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione SEPHAROSE™ beads (Sigma Chemical; St. Louis, Mo.) or glutathione derivatized microtiter plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized using conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283, 317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease. By way of example, the gene encoding h-ig6p maps to human chromosome 2, as assessed by alignment of the h-ig6p cDNA sequence with known human genomic sequence fragments. Aberrant expression or activity of h-ig6p can thus be associated with a disorder attributable to a genomic lesion that maps to this region of chromosome 2.

Briefly, genes can be mapped to chromosomes by preparing PCR primers (preferably 15–25 base pairs in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) Science 220:919–924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sub-localization can be achieved with panels of fragments from specific chromosomes. Other mapping strategies which can similarly be used to map a gene to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al. (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to non-coding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Furthermore, the nucleic acid sequences disclosed herein can be used to perform searches against "mapping databases", e.g., BLAST-type search, such that the chromosome position of the gene is identified by sequence homology or identity with known sequence fragments which have been mapped to chromosomes.

A polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) Cytogenet. Cell Genet. 47:37–41 and Van Keuren et al. (1986) Hum. Genet. 74:34–40. Alternatively, the presence of the polypeptide in the somatic cell hybrids can be determined by assaying an activity or property of the polypeptide, for example, enzymatic activity, as described in Bordelon-Riser et al. (1979) Somatic Cell Genetics 5:597–613 and Owerbach et al. (1978) Proc. Natl. Acad. Sci. USA 75:5640–5644.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "dog tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the non-coding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of SEQ ID NO: 1 (or the nucleotide sequence of the clone deposited with ATCC® on Jul. 28, 2000 as accession number PTA-2282) can comfortably provide positive individual identification with a panel of perhaps 10 or more primers which each yield a non-coding amplified sequence of 100 bases. If predicted coding sequences, such as those in SEQ ID NO: 2, are used, a more appropriate number of primers for positive individual identification would be higher.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to non-coding regions are particularly appropriate for this use as greater numbers of polymorphisms occur in the non-coding regions, making it easier to differentiate individuals using this technique. Examples of polynucleotide reagents include the nucleic acid sequences of the invention or portions thereof, e.g., fragments derived from non-coding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining h-ig6p protein and/or nucleic acid expression as well as h-ig6p activity, in the context of a biological sample (e.g., blood, serum, cells, tissue) to thereby determine whether an individual is afflicted with a disease or disorder, or is at risk of developing a disorder, associated with aberrant or unwanted h-ig6p expression or activity. The invention also provides for prognostic (or predictive) assays for determining whether an individual is at risk of developing a disorder associated with h-ig6p protein, nucleic acid expression or activity. For example, mutations in a h-ig6p gene can be assayed in a biological sample. Such assays can be used for prognostic or predictive purpose to thereby prophylactically treat an individual prior to the onset of a disorder characterized by or associated with h-ig6p protein, nucleic acid expression or activity.

As an alternative to making determinations based on the absolute expression level of selected genes, determinations can be based on the normalized expression levels of these genes. Expression levels are normalized by correcting the absolute expression level of a h-ig6p gene by comparing its expression to the expression of a gene that is not a h-ig6p gene, e.g., a housekeeping gene that is constitutively expressed. Suitable genes for normalization include housekeeping genes such as the actin gene. This normalization allows the comparison of the expression level in one sample, e.g., a patient sample, to another sample, e.g., a sample obtained from a non-diseased source, or between samples from different sources.

Alternatively, the expression level can be provided as a relative expression level. To determine a relative expression level of a gene, the level of expression of the gene is determined for 10 or more samples of different pancreatic islet of Langerhans cell isolates, preferably 50 or more samples, prior to the determination of the expression level for the sample in question. The mean expression level of each of the genes assayed in the larger number of samples is determined and this is used as a baseline expression level for the gene(s) in question. The expression level of the gene determined for the test sample (absolute level of expression) is then divided by the mean expression value obtained for that gene. This provides a relative expression level and aids in identifying extreme cases of a disorder associated with aberrant activity or expression of h-ig6p.

Preferably, the samples used in the baseline determination are obtained from diseased or from non-diseased cells of pancreatic tissue (preferably islet of Langerhans cells or isolated alpha or beta islet cells). The choice of the cell source is dependent on the use of the relative expression level. Using expression found in normal tissues as a mean expression score aids in validating whether the h-ig6p gene assayed is diseased cell-specific (versus normal cells). Such a use is particularly important in identifying whether a h-ig6p gene can serve as a target gene. In addition, as more data is accumulated, the mean expression value can be revised, providing improved relative expression values based on accumulated data. Expression data from pancreatic islet cells provides a means for grading the severity of the disease state.

Another aspect of the invention pertains to monitoring the influence of agents (e.g., drugs, compounds) on the expression or activity of h-ig6p in clinical trials.

These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO: 1, the nucleotide sequence of the clone deposited with ATCC® on Jul. 28, 2000 as accession number PTA-2282, or a portion thereof, such as an oligonucleotide of at least 15, 30, 50, 100, 250 or 500 nucleotides in length and sufficient to specifically hybridize under stringent conditions with a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention (e.g., a proliferative disorder, e.g., psoriasis or cancer). For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

By way of example, abnormally high levels of expression of h-ig6p in a human can be an indication that the human is afflicted with, or is susceptible to, a disorder associated with aberrantly low insulin secretion, such as diabetes or obesity. Alternatively, abnormally low levels of expression of h-ig6p in a human can be an indication that the human is afflicted with, or is susceptible to, a disorder associated with aberrantly high insulin secretion, such as hyperinsulinemia. Thus, compositions and kits as described herein can be made and used for diagnosis and prognostication of these and other disorders associated with pancreatic and metabolic disorders.

2. Prognostic Assays

The methods described herein can furthermore be used as diagnostic or prognostic assays to identify subjects having or at risk of developing a disease or disorder associated with aberrant expression or activity of a polypeptide of the invention. For example, the assays described herein, such as the preceding diagnostic assays or the following assays, can be used to identify a subject having or at risk of developing a disorder associated with aberrant expression or activity of a polypeptide of the invention, e.g., a proliferative disorder, e.g., psoriasis or cancer, or an angiogenic disorder. Alternatively, the prognostic assays can be used to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in a gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR can be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be used when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in a selected gene include methods in which protection from cleavage agents is used to detect mismatched bases in RNA/RNA or RNA/DNA heteroduplexes (Myers et al. (1985) Science 230:1242). In general, the technique of mismatch cleavage entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) Proc. Natl. Acad. Sci. USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called DNA mismatch repair enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) can be used to detect differences in electrophoretic mobility between mutant and wild type nucleic acids (Orita et al. (1989) Proc. Natl. Acad. Sci. USA 86:2766; see also Cotton (1993) Mutat. Res. 285:125–144; Hayashi (1992) Genet. Anal. Tech. Appl. 9:73–79). Single-stranded DNA fragments of sample and control nucleic acids will be denatured and allowed to re-nature. The secondary structure of single-stranded nucleic acids varies according to sequence, and the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method uses heteroduplex analysis to separate double stranded heteroduplex molecules on the basis of changes in electrophoretic mobility (Keen et al. (1991) Trends Genet. 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 base pairs of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers can be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent or reduce polymerase extension (Prossner (1993) Tibtech 11:238). In addition, it can be desirable to introduce a novel restriction site in the region of the mutation to create cleavage-based detection (Gasparini et al. (1992) Mol. Cell Probes 6:1). It is anticipated that in certain embodiments amplification can also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein can be performed, for example, by using pre-packaged diagnostic kits comprising at least one probe nucleic acid or antibody reagent described herein, which can be conveniently used, e.g., in clinical settings to diagnose patients exhibiting symptoms or family history of a disease or illness involving a gene encoding a polypeptide of the invention. Furthermore, any cell type or tissue, preferably peripheral blood leukocytes, in which the polypeptide of the invention is expressed can be used in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual can be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses.

If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drugs, compounds) on the expression or activity of a polypeptide of the invention (e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state can be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the pre-administration sample; (iii) obtaining one or more post-administration samples from the subject; (iv) detecting the level the of the polypeptide or nucleic acid of the invention in the post-administration samples; (V) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent can be desirable to increase the expression or activity of the polypeptide to higher levels than detected, i.e., to increase the effectiveness of the agent. Alternatively, decreased administration of the agent can be desirable to decrease expression or activity of the polypeptide to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant expression or activity of a polypeptide of the invention. For example, disorders characterized by aberrant expression or activity of the polypeptides of the invention include proliferative disorders such as cancer. Aberrant expression or activity of h-ig6p can be associated with disorders of the pancreas, including for example, metabolic disorders such as disorders of carbohydrate metabolism (e.g., diabetes, hyperinsulinemia, and obesity). By inhibiting h-ig6p expression or activity, insulin secretion can be enhanced, and disorders such as diabetes or obesity can be alleviated, inhibited, or prevented. By enhancing h-ig6p expression or activity, insulin secretion can be inhibited, and disorders such as hyperinsulinemia can be alleviated, inhibited, or prevented. Enhancing or inhibiting h-ig6p expression can also affect the sensitivity of cell signaling mechanisms for intracellular and extracellular glucose/G6P, and disorders associated with aberrant cell signaling relating to these levels can be alleviated, inhibited, or prevented.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrance, such that a disease or disorder is prevented or, alternatively, delayed in its progression. Depending on the type of aberrance, for example, an agonist or antagonist agent can be used for treating the subject. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., enhances or inhibits) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or depressed and/or in which increased activity is likely to have a beneficial effect. Conversely, inhibition of activity is desirable in situations in which activity or expression is abnormally high or enhanced and/or in which decreased activity is likely to have a beneficial effect.

The contents of all references, patents and published patent applications cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide comprising the amino acid sequence of SEQ ID NO:3.

2. The polypeptide of claim 1 further comprising heterologous amino acid sequences.

3. An isolated polypeptide comprising the amino acid sequence encoded by any one of the nucleotide sequence of SEQ ID NO:1 or the nucleotide sequence of SEQ ID NO:2, or the amino acid sequence encoded by the nucleotide sequence of the clone deposited with American Type Culture Collection on Jul. 28, 2000 as accession number PTA-2282.

4. The polypeptide of claim 3 further comprising heterologous amino acid sequences.

5. An isolated polypeptide comprising a fragment of a polypeptide having the amino acid sequence SEQ ID NO: 3 or the amino acid sequence encoded by the clone deposited with ATCC® on Jul. 28, 2000 as accession number PTA-2282, wherein the sequence of the fragment comprises at least 60 consecutive amino acid residues of SEQ ID NO: 3 or the amino acid sequence encode by the clone deposited with ATCC® on Jul. 28, 2000 as accession number PTA-2282 and wherein the polypeptide or the fragment of the polypeptide has human pancreatic islet cell-specific glucose-6-phosphatase (h-ig6p) activity.

6. The polypeptide of claim 5 further comprising heterologous amino acid sequences.

7. An isolated polypeptide comprising a polypeptide which is encoded by a nucleic acid molecule having a nucleotide sequence which is at least 91% identical to a nucleic acid molecule having a sequence comprising SEQ ID NO: 1 or 2 or the nucleotide sequence of the clone deposited with ATCC® on Jul. 28, 2000 as accession number PTA-2282, wherein the polypeptide has human pancreatic islet cell-specific glucose-6-phosphatase (h-ig6p) activity.

8. The polypeptide of claim 7 further comprising heterologous amino acid sequences.

* * * * *

SEQUENCE LISTING

```
<160> NUMBER OF SEQ ID NOS: 27

<210> SEQ ID NO 1
<211> LENGTH: 1138
<212> TYPE: DNA
<213> ORGANISM: Homo sapiens

<400> SEQUENCE: 1
aattcgccct tcagctccaa ttgctctatg tttagaattg cctctttttc aagatggatt      60
tccttcacag gaatggagtg ctcataattc agcatttgca gaaggactac cgagcttact     120 acactttct  aaattttatg tccaatgttg gagaccccag gaatatcttt ttcatttatt     180
ttccactttg ttttcaattt aatcagacag ttggaaccaa gatgatatgg gtagcagtca     240
ttggggattg gttaaatctt atatttaaat ggatattatt tggtcatcga ccttactggt     300
gggtccaaga aactcagatt tacccaaatc actcaagtcc atgccttgaa cagttccta    360 ctacatgtga aacaggtcca ggaagtccat ctggccatgc aatgggcgca tcctgtgtct     420
ggtatgtcat ggtaaccgct gccctgagcc acactgtctg tgggatggat aagttctcta     480
tcactctgca cagactgacc tggtcatttc tttggagtgt tttttggttg attcaaatca     540
gtgtctgcat ctccagagta ttcatagcaa cacattttcc tcatcaagtt attcttggag     600
taattggtgg catgctggtg gcagaggcct ttgaacacac tccaggcatc caaacggcca     660
gtctgggcac atacctgaag accaacctct ttctcttcct gtttgcagtt ggcttttacc     720
tgcttcttag ggtgctcaac attgacctgc tgtggtccgt gcccatagcc aaaaagtggt     780
gtgctaaccc cgactggatc cacattgaca ccacgccttt tgctggactc gtgagaaacc     840 ttgggggtcct ctttggcttg ggctttgcaa tcaactcaga gatgttcctc ctgagctgcc     900
gagggggaaa taactacaca ctgagcttcc ggttgctctg tgccttgacc tcattgacaa     960
tactgcagct ctaccatttc ctccagatcc cgactcacga agagcattta ttttatgtgc    1020
```

```
tgtcttttg taaaagtgca tccattcccc taactgtggt tgctttcatt ccctactctg    1080
ttcatatgtt aatgaaacaa agcggaaaga agagtcagta gaaaaaaaaa aaaaaaaa     1138

<210> SEQ ID NO 2
<211> LENGTH: 1065
<212> TYPE: DNA
<213> ORGANISM: Homo sapiens

<400> SEQUENCE: 2
atggatttcc ttcacaggaa tggagtgctc ataattcagc atttgcagaa ggactaccga     60
gcttactaca cttttctaaa ttttatgtcc aatgttggag accccaggaa tatctttttc    120
atttattttc cactttgttt tcaatttaat cagacagttg gaaccaagat gatatgggta    180
gcagtcattg gggattggtt aaatcttata tttaaatgga tattatttgg tcatcgacct    240
tactggtggg tccaagaaac tcagatttac ccaaatcact caagtccatg ccttgaacag    300
ttccctacta catgtgaaac aggtccagga agtccatctg ccatgcaat gggcgcatcc    360 tgtgtctggt atgtcatggt aaccgctgcc ctgagccaca ctgtctgtgg gatggataag    420
ttctctatca ctctgcacag actgacctgg tcatttcttt ggagtgtttt ttggttgatt    480
caaatcagtg tctgcatctc cagagtattc atagcaacac attttcctca tcaagttatt    540
cttggagtaa ttggtggcat gctggtggca gaggcctttg aacacactcc aggcatccaa    600
acggccagtc tgggcacata cctgaagacc aacctctttc tcttcctgtt tgcagttggc    660
ttttacctgc ttcttagggt gctcaacatt gacctgctgt ggtccgtgcc catagccaaa    720
aagtggtgtg ctaaccccga ctggatccac attgacacca cgccttttgc tggactcgtg    780
agaaaccttg gggtcctctt tggcttgggc tttgcaatca actcagagat gttcctcctg    840
agctgccgag ggggaaataa ctacacactg agcttccggt tgctctgtgc cttgacctca    900
ttgacaatac tgcagctcta ccatttcctc cagatcccga ctcacgaaga gcatttattt    960
tatgtgctgt ctttttgtaa aagtgcatcc attcccctaa ctgtggttgc tttcattccc   1020
tactctgttc atatgttaat gaaacaaagc ggaagaaga gtcag                     1065

<210> SEQ ID NO 3
<211> LENGTH: 355
<212> TYPE: PRT
<213> ORGANISM: Homo sapiens

<400> SEQUENCE: 3

Met Asp Phe Leu His Arg Asn Gly Val Leu Ile Ile Gln His Leu Gln
  1               5                  10                  15

Lys Asp Tyr Arg Ala Tyr Tyr Thr Phe Leu Asn Phe Met Ser Asn Val
             20                  25                  30

Gly Asp Pro Arg Asn Ile Phe Phe Ile Tyr Phe Pro Leu Cys Phe Gln
         35                  40                  45

Phe Asn Gln Thr Val Gly Thr Lys Met Ile Trp Val Ala Val Ile Gly
     50                  55                  60

Asp Trp Leu Asn Leu Ile Phe Lys Trp Ile Leu Phe Gly His Arg Pro
 65                  70                  75                  80

Tyr Trp Trp Val Gln Glu Thr Gln Ile Tyr Pro Asn His Ser Ser Pro
                 85                  90                  95

Cys Leu Glu Gln Phe Pro Thr Thr Cys Glu Thr Gly Pro Gly Ser Pro
            100                 105                 110

Ser Gly His Ala Met Gly Ala Ser Cys Val Trp Tyr Val Met Val Thr
        115                 120                 125
```

```
Ala Ala Leu Ser His Thr Val Cys Gly Met Asp Lys Phe Ser Ile Thr
        130                 135                 140
Leu His Arg Leu Thr Trp Ser Phe Leu Trp Ser Val Phe Trp Leu Ile
145                 150                 155                 160
Gln Ile Ser Val Cys Ile Ser Arg Val Phe Ile Ala Thr His Phe Pro
                165                 170                 175
His Gln Val Ile Leu Gly Val Ile Gly Gly Met Leu Val Ala Glu Ala
                180                 185                 190
Phe Glu His Thr Pro Gly Ile Gln Thr Ala Ser Leu Gly Thr Tyr Leu
            195                 200                 205
Lys Thr Asn Leu Phe Leu Phe Leu Phe Ala Val Gly Phe Tyr Leu Leu
210                 215                 220
Leu Arg Val Leu Asn Ile Asp Leu Leu Trp Ser Val Pro Ile Ala Lys
225                 230                 235                 240
Lys Trp Cys Ala Asn Pro Asp Trp Ile His Ile Asp Thr Thr Pro Phe
                245                 250                 255
Ala Gly Leu Val Arg Asn Leu Gly Val Leu Phe Gly Leu Gly Phe Ala
                260                 265                 270
Ile Asn Ser Glu Met Phe Leu Leu Ser Cys Arg Gly Gly Asn Asn Tyr
                275                 280                 285
Thr Leu Ser Phe Arg Leu Leu Cys Ala Leu Thr Ser Leu Thr Ile Leu
            290                 295                 300
Gln Leu Tyr His Phe Leu Gln Ile Pro Thr His Glu Glu His Leu Phe
305                 310                 315                 320
Tyr Val Leu Ser Phe Cys Lys Ser Ala Ser Ile Pro Leu Thr Val Val
                325                 330                 335
Ala Phe Ile Pro Tyr Ser Val His Met Leu Met Lys Gln Ser Gly Lys
                340                 345                 350
Lys Ser Gln
        355

<210> SEQ ID NO 4
<211> LENGTH: 355
<212> TYPE: PRT
<213> ORGANISM: Mus musculus

<400> SEQUENCE: 4

Met Asp Phe Leu His Arg Ser Gly Val Leu Ile Ile His His Leu Gln
  1               5                  10                  15
Glu Asp Tyr Arg Thr Tyr Tyr Gly Phe Leu Asn Phe Met Ser Asn Val
                20                  25                  30
Gly Asp Pro Arg Asn Ile Phe Ser Ile Tyr Phe Pro Leu Trp Phe Gln
            35                  40                  45
Leu Asn Gln Asn Val Gly Thr Lys Met Ile Trp Val Ala Val Ile Gly
        50                  55                  60
Asp Trp Phe Asn Leu Ile Phe Lys Trp Ile Leu Phe Gly His Arg Pro
65                  70                  75                  80
Tyr Trp Trp Ile Gln Glu Thr Glu Ile Tyr Pro Asn His Ser Ser Pro
                85                  90                  95
Cys Leu Glu Gln Phe Pro Thr Thr Cys Glu Thr Gly Pro Gly Ser Pro
                100                 105                 110
Ser Gly His Ala Met Gly Ser Ser Cys Val Trp Tyr Val Met Val Thr
            115                 120                 125
Ala Ala Leu Ser Tyr Thr Ile Ser Arg Met Glu Glu Ser Ser Val Thr
```

```
              130                 135                 140
Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
                180                 185                 190

Phe Glu His Thr Pro Gly Val His Met Ala Ser Leu Ser Val Tyr Leu
                195                 200                 205

Lys Thr Asn Val Phe Leu Phe Leu Phe Ala Leu Gly Phe Tyr Leu Leu
                210                 215                 220

Leu Arg Leu Phe Gly Ile Asp Leu Leu Trp Ser Val Pro Ile Ala Lys
225                 230                 235                 240

Lys Trp Cys Ala Asn Pro Asp Trp Ile His Ile Asp Ser Thr Pro Phe
                245                 250                 255

Ala Gly Leu Val Arg Asn Leu Gly Val Leu Phe Gly Leu Gly Phe Ala
                260                 265                 270

Ile Asn Ser Glu Met Phe Leu Arg Ser Cys Gln Gly Glu Asn Gly Thr
                275                 280                 285

Lys Pro Ser Phe Arg Leu Leu Cys Ala Leu Thr Ser Leu Thr Thr Met
290                 295                 300

Gln Leu Tyr Arg Phe Ile Lys Ile Pro Thr His Ala Glu Pro Leu Phe
305                 310                 315                 320

Tyr Leu Leu Ser Phe Cys Lys Ser Ala Ser Ile Pro Leu Met Val Val
                325                 330                 335

Ala Leu Ile Pro Tyr Cys Val His Met Leu Met Arg Pro Gly Asp Lys
                340                 345                 350

Lys Thr Lys
        355

<210> SEQ ID NO 5
<211> LENGTH:
<212> TYPE:
<213> ORGANISM:

<400> SEQUENCE: 5

000

<210> SEQ ID NO 6
<211> LENGTH:
<212> TYPE:
<213> ORGANISM:

<400> SEQUENCE: 6

000

<210> SEQ ID NO 7
<211> LENGTH:
<212> TYPE:
<213> ORGANISM:

<400> SEQUENCE: 7

000

<210> SEQ ID NO 8
<211> LENGTH:
<212> TYPE:
<213> ORGANISM:
```

-continued

<400> SEQUENCE: 8

000

<210> SEQ ID NO 9
<211> LENGTH:
<212> TYPE:
<213> ORGANISM:

<400> SEQUENCE: 9

000

<210> SEQ ID NO 10
<211> LENGTH:
<212> TYPE:
<213> ORGANISM:

<400> SEQUENCE: 10

000

<210> SEQ ID NO 11
<211> LENGTH:
<212> TYPE:
<213> ORGANISM:

<400> SEQUENCE: 11

000

<210> SEQ ID NO 12
<211> LENGTH:
<212> TYPE:
<213> ORGANISM:

<400> SEQUENCE: 12

000

<210> SEQ ID NO 13
<211> LENGTH:
<212> TYPE:
<213> ORGANISM:

<400> SEQUENCE: 13

000

<210> SEQ ID NO 14
<211> LENGTH:
<212> TYPE:
<213> ORGANISM:

<400> SEQUENCE: 14

000

<210> SEQ ID NO 15
<211> LENGTH:
<212> TYPE:
<213> ORGANISM:

<400> SEQUENCE: 15

000

<210> SEQ ID NO 16
<211> LENGTH:
<212> TYPE:

```
<213> ORGANISM:

<400> SEQUENCE: 16

000

<210> SEQ ID NO 17
<211> LENGTH:
<212> TYPE:
<213> ORGANISM:

<400> SEQUENCE: 17

000

<210> SEQ ID NO 18
<211> LENGTH:
<212> TYPE:
<213> ORGANISM:

<400> SEQUENCE: 18

000

<210> SEQ ID NO 19
<211> LENGTH:
<212> TYPE:
<213> ORGANISM:

<400> SEQUENCE: 19

000

<210> SEQ ID NO 20
<211> LENGTH:
<212> TYPE:
<213> ORGANISM:

<400> SEQUENCE: 20

000

<210> SEQ ID NO 21
<211> LENGTH:
<212> TYPE:
<213> ORGANISM:

<400> SEQUENCE: 21

000

<210> SEQ ID NO 22
<211> LENGTH: 1901
<212> TYPE: DNA
<213> ORGANISM: Mus musculus

<400> SEQUENCE: 22
tagagacagt gggacacagg gccctgcagt tccacctgct tcatgcttag acctgcatca      60
agatggattt ccttcatagg agtggagtgc ttattattca tcatctgcag gaggactacc     120
ggacttacta tggttttcta aattttatgt ccaatgttgg agaccccga aatatctttt      180 ctatttactt cccactttgg tttcagttga atcagaatgt tggaaccaag atgatctggg     240
tagcggtcat aggggactgg ttcaatctca tatttaaatg gatattgttt ggccatcgtc     300
cttactggtg gatacaagaa actgagattt atccaaatca ttcaagccca tgtcttgagc     360
agtttcctac tacgtgtgaa acaggcccag gaagtccatc tggccacgca atgggctcat     420
cgtgcgtctg gtatgtcatg gtaacagctg ccctaagcta caccatcagc cggatggagg     480
```

```
agtcctctgt cactctgcac agactgacct ggtcctttct gtggagtgtt ttctggttga    540
ttcaaatcag cgtctgcatc tcaagagtat tcatagccac acatttcccc catcaggtca    600
ttcttggagt gattggtggg atgctagtag ccgaggcctt gaacacact ccaggagtcc     660 acatggccag cttgagtgtg tacctgaaga ccaacgtctt cctcttcctg tttgccctcg    720
gcttttacct gcttctccga ctgttcggta ttgacctgct gtggtccgtg cccatcgcca    780
aaaagtggtg tgccaaccca gactggatcc acattgacag cacgcctttt gctggactcg    840
tgagaaacct cggggtcctc tttggcttgg gtttcgccat caactcagaa atgttccttc    900
ggagctgcca gggagaaaat ggcaccaagc cgagcttccg cttgctctgt gctctgacct    960
cactgaccac aatgcaactt tatcgcttca tcaagatccc gactcacgcg gaacctttat   1020
tttacctgtt gtctttctgt aaaagtgcgt ccatcccccct gatggtggtg gctctaattc  1080
cctactgtgt acatatgtta atgagacccg gtgacaagaa gactaaatag agctgcagtg   1140
ccctgtggtc tgaggatcac ctactttctg ttttcctcaa tagagccaca gcacagagac   1200
tgggagcgtc tctacagagg tcacaccatg atgaccaaag tcctgctcc acccacagac    1260 atgtttagtc tgctttccaa gtggcattta aaaataaca gtatttaacc agaaagtcca    1320
tattttcttg acaaaactga caatacggta acatatgaga gatggtataa cccatgtaaa   1380
gacagttgac aggggctgga tgcttacatt ccagttagca gaaagactcc ttctaatcat   1440
agtatttagc agtcaacaaa accccagga gctgatgttt ctatcatctt aaagtctggc    1500
tacttcaggc tcctgtggac cacttagaag tgaccacggt ctactttac ttttaggagt    1560 caattctttc aaaattctca tgtatcagat aaggaaatag aggtttgttc agatcaagta   1620
acttgactgt aatagtgcag ggttgaaacc agagttggaa cacaaggctt ctgatacata   1680
tatctctata agaatgcttt cttctttct ttttagggag ttaaaaaaaa agagcaaatg    1740
catgtattta aaatctatgt ttgccatcta aaacacccat cttttcagaa atggcattgg   1800
aatgctacat tctgcttgac ttatgctcag agtacagtgt cttttccagg ctagcaatgg   1860
ctgtatatat ttcaataaac gctgctgaaa acaacccact g                       1901
```

<210> SEQ ID NO 23
<211> LENGTH: 355
<212> TYPE: PRT
<213> ORGANISM: Mus musculus

<400> SEQUENCE: 23

```
Met Asp Phe Leu His Arg Ser Gly Val Leu Ile Ile His His Leu Gln
 1               5                  10                  15

Glu Asp Tyr Arg Thr Tyr Tyr Gly Phe Leu Asn Phe Met Ser Asn Val
                20                  25                  30

Gly Asp Pro Arg Asn Ile Phe Ser Ile Tyr Phe Pro Leu Trp Phe Gln
        35                  40                  45

Leu Asn Gln Asn Val Gly Thr Lys Met Ile Trp Val Ala Val Ile Gly
    50                  55                  60

Asp Trp Phe Asn Leu Ile Phe Lys Trp Ile Leu Phe Gly His Arg Pro
65                  70                  75                  80

Tyr Trp Trp Ile Gln Glu Thr Glu Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ser Ser Cys Val Trp Tyr Val Met Val Thr
```

```
                115                 120                 125
Ala Ala Leu Ser Tyr Thr Ile Ser Arg Met Glu Glu Ser Ser Val Thr
        130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190

Phe Glu His Thr Pro Gly Val His Met Ala Ser Leu Ser Val Tyr Leu
        195                 200                 205

Lys Thr Asn Val Phe Leu Phe Leu Phe Ala Leu Gly Phe Tyr Leu Leu
210                 215                 220

Leu Arg Leu Phe Gly Ile Asp Leu Leu Trp Ser Val Pro Ile Ala Lys
225                 230                 235                 240

Lys Trp Cys Ala Asn Pro Asp Trp Ile His Ile Asp Ser Thr Pro Phe
                245                 250                 255

Ala Gly Leu Val Arg Asn Leu Gly Val Leu Phe Gly Leu Gly Phe Ala
            260                 265                 270

Ile Asn Ser Glu Met Phe Leu Arg Ser Cys Gln Gly Glu Asn Gly Thr
        275                 280                 285

Lys Pro Ser Phe Arg Leu Leu Cys Ala Leu Thr Ser Leu Thr Thr Met
290                 295                 300

Gln Leu Tyr Arg Phe Ile Lys Ile Pro Thr His Ala Glu Pro Leu Phe
305                 310                 315                 320

Tyr Leu Leu Ser Phe Cys Lys Ser Ala Ser Ile Pro Leu Met Val Val
                325                 330                 335

Ala Leu Ile Pro Tyr Cys Val His Met Leu Met Arg Pro Gly Asp Lys
            340                 345                 350

Lys Thr Lys
        355

<210> SEQ ID NO 24
<211> LENGTH: 352
<212> TYPE: PRT
<213> ORGANISM: Haplochromis nubilis

<400> SEQUENCE: 24

Met Asp Leu Leu His Ser Trp Gly Val Glu Leu Ala Val Tyr Leu Gln
  1               5                  10                  15

Thr Arg Tyr Gly Lys Tyr Glu Gly Leu Phe Asp Leu Ala Ser Thr Val
             20                  25                  30

Ala Asp Leu His Thr Thr Phe Phe Trp Leu Phe Pro Ile Trp Phe His
         35                  40                  45

Leu Arg Arg Asp Thr Ala Leu Arg Leu Ile Trp Val Ala Val Ile Gly
 50                  55                  60

Asp Trp Leu Asn Leu Val Leu Lys Trp Val Leu Phe Gly Glu Arg Pro
 65                  70                  75                  80

Tyr Trp Trp Val His Glu Thr Lys Phe Tyr Gly Ala Gly Pro Ala Pro
                 85                  90                  95

Ser Leu Gln Gln Phe Pro Ile Thr Cys Glu Thr Gly Pro Gly Ser Pro
            100                 105                 110

Ser Gly His Ala Met Gly Ala Ala Gly Val Trp Tyr Val Met Val Thr
        115                 120                 125
```

Ala Leu Leu Ser Ile Ala Arg Glu Lys Gln Cys Pro Pro Leu Leu Tyr
    130                 135                 140

Arg Phe Leu Tyr Ile Gly Leu Trp Met Leu Met Gly Leu Val Glu Leu
145                 150                 155                 160

Val Val Cys Ile Ser Arg Val Tyr Met Ala Ala His Phe Pro His Gln
                165                 170                 175

Val Ile Ala Gly Ile Ile Thr Gly Thr Leu Val Ala Glu Val Val Ser
            180                 185                 190

Lys Glu Lys Trp Ile Tyr Ser Ala Ser Leu Lys Lys Tyr Phe Leu Ile
        195                 200                 205

Thr Leu Phe Leu Thr Ser Phe Ala Val Gly Phe Tyr Val Leu Leu Lys
    210                 215                 220

Ala Leu Asp Val Asp Leu Leu Trp Thr Met Glu Lys Ala Gln Lys Trp
225                 230                 235                 240

Cys Ile Arg Pro Glu Trp Val His Leu Asp Ser Ala Pro Phe Ala Ser
                245                 250                 255

Leu Leu Arg Asn Met Gly Ser Leu Phe Gly Leu Gly Leu Gly Leu His
            260                 265                 270

Ser Pro Phe Tyr Lys Thr Thr Lys Met Arg Ile Met Ser Ala Pro Leu
        275                 280                 285

Arg Ile Gly Cys Ile Val Ile Ser Val Ser Leu Leu His Leu Leu Asp
    290                 295                 300

Gly Trp Thr Phe Ser Pro Glu Asn His Met Thr Phe Tyr Ala Leu Ser
305                 310                 315                 320

Phe Gly Lys Ser Ala Val Ala Leu Leu Ile Pro Thr Thr Leu Val Pro
                325                 330                 335

Trp Ala Leu Ser Lys Ile Tyr Pro Val Lys Thr Glu Gly Lys Asn Leu
            340                 345                 350

<210> SEQ ID NO 25
<211> LENGTH: 357
<212> TYPE: PRT
<213> ORGANISM: Mus sp.

<400> SEQUENCE: 25

Met Glu Glu Gly Met Asn Ile Leu His Asp Phe Gly Ile Gln Ser Thr
1               5                   10                  15

Arg Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Lys Glu Thr Val Gly Ile Asn Leu Leu Trp Val
    50                  55                  60

Ala Val Val Gly Asp Trp Phe Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Ser Ser Val Pro Ile Ile Lys Gln Phe Pro Val Thr Cys Glu Thr Gly
            100                 105                 110

Pro Gly Ser Pro Ser Gly His Ala Met Gly Ala Ala Gly Val Tyr Tyr
        115                 120                 125

Val Met Val Thr Ser Thr Leu Ala Ile Phe Arg Gly Lys Lys Lys Pro
    130                 135                 140

Thr Tyr Gly Phe Arg Cys Leu Asn Val Ile Leu Trp Leu Gly Phe Trp
145                 150                 155                 160

```
Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile Arg Gly Ile Tyr Asn Ala Ser Leu Arg Lys
        195                 200                 205

Tyr Cys Leu Ile Thr Ile Phe Leu Phe Gly Phe Ala Leu Gly Phe Tyr
    210                 215                 220

Leu Leu Leu Lys Gly Leu Gly Val Asp Leu Leu Trp Thr Leu Glu Lys
225                 230                 235                 240

Ala Lys Arg Trp Cys Glu Arg Pro Glu Trp Val His Leu Asp Thr Thr
                245                 250                 255

Pro Phe Ala Ser Leu Phe Lys Asn Leu Gly Thr Leu Leu Gly Leu Gly
            260                 265                 270

Leu Ala Leu Asn Ser Ser Met Tyr Arg Lys Ser Cys Lys Gly Glu Leu
        275                 280                 285

Ser Lys Ser Phe Pro Phe Arg Phe Ala Cys Ile Val Ala Ser Leu Val
    290                 295                 300

Leu Leu His Leu Phe Asp Ser Leu Lys Pro Pro Ser Gln Val Glu Leu
305                 310                 315                 320

Ile Phe Tyr Ile Leu Ser Phe Cys Lys Ser Ala Thr Val Pro Phe Ala
                325                 330                 335

Ser Val Ser Leu Ile Pro Tyr Cys Leu Ala Arg Ile Leu Gly Gln Thr
            340                 345                 350

His Lys Lys Ser Leu
        355

<210> SEQ ID NO 26
<211> LENGTH: 357
<212> TYPE: PRT
<213> ORGANISM: Canis familiaris

<400> SEQUENCE: 26

Met Glu Lys Gly Met Asp Val Leu His Asp Phe Gly Ile Gln Ser Thr
  1               5                  10                  15

His Tyr Leu Gln Val Asn Tyr Gln Asp Ser Gln Asp Trp Phe Ile Leu
             20                  25                  30

Val Ser Val Ile Ala Asp Leu Arg Asn Ala Phe Tyr Val Leu Phe Pro
         35                  40                  45

Ile Trp Phe His Leu Arg Glu Ala Val Gly Ile Lys Leu Leu Trp Val
     50                  55                  60

Ala Val Ile Gly Asp Trp Leu Asn Leu Val Phe Lys Trp Ile Leu Phe
 65                  70                  75                  80

Gly Gln Arg Pro Tyr Trp Trp Val Met Asp Thr Asp Tyr Tyr Ser Asn
                 85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Arg Gly Arg Lys Arg Pro
    130                 135                 140

Thr Tyr Arg Phe Arg Cys Leu Asn Ile Leu Leu Trp Leu Gly Phe Trp
145                 150                 155                 160

Ala Val Gln Leu Asn Val Cys Leu Ser Arg Ile Tyr Leu Ala Ala His
```

```
                    165                 170                 175
Phe Pro His Gln Val Ala Gly Val Leu Ser Gly Ile Ala Val Ala
                180                 185                 190

Glu Thr Phe Arg His Ile Gln Ser Ile Tyr Asn Ala Ser Leu Lys Lys
                195                 200                 205

Tyr Phe Leu Ile Thr Phe Phe Leu Phe Ser Phe Ala Ile Gly Phe Tyr
            210                 215                 220

Leu Leu Leu Lys Gly Leu Gly Val Asp Leu Leu Trp Thr Leu Glu Lys
225                 230                 235                 240

Ala Arg Arg Trp Cys Glu Arg Pro Glu Trp Val His Ile Asp Thr Thr
                    245                 250                 255

Pro Phe Ala Ser Leu Leu Lys Asn Val Gly Thr Leu Phe Gly Leu Gly
                260                 265                 270

Val Thr Leu Asn Ser Ser Met Tyr Arg Glu Ser Cys Lys Gly Lys Leu
            275                 280                 285

Ser Lys Trp Phe Pro Phe Arg Leu Ser Cys Ile Val Val Ser Leu Ile
            290                 295                 300

Leu Leu His Leu Phe Asp Ser Leu Lys Pro Pro Ser Gln Thr Glu Leu
305                 310                 315                 320

Ile Phe Tyr Thr Leu Ser Phe Cys Lys Ser Ala Ala Val Pro Leu Ala
                    325                 330                 335

Ser Val Ser Leu Ile Pro Tyr Cys Leu Ala Arg Val Phe Asp Gln Pro
                340                 345                 350

Asp Lys Lys Ser Leu
                355

<210> SEQ ID NO 27
<211> LENGTH: 357
<212> TYPE: PRT
<213> ORGANISM: Homo sapiens

<400> SEQUENCE: 27

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
                20                  25                  30

Val Ser Val Ile Ala Asp Leu Arg Asn Ala Phe Tyr Val Leu Phe Pro
            35                  40                  45

Ile Trp Phe His Leu Gln Glu Ala Val Gly Ile Lys Leu Leu Trp Val
        50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
                100                 105                 110

Pro Gly Ser Pro Ser Gly His Ala Met Gly Thr Ala Gly Val Tyr Tyr
            115                 120                 125

Val Met Val Thr Ser Thr Leu Ser Ile Phe Gln Gly Lys Ile Lys Pro
130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175
```

-continued

```
Phe Pro His Gln Val Val Ala Gly Val Leu Ser Gly Ile Ala Val Thr
            180             185                 190

Glu Thr Phe Ser His Ile His Ser Ile Tyr Asn Ala Ser Leu Lys Lys
        195             200                 205

Tyr Phe Leu Ile Thr Phe Phe Leu Phe Ser Phe Ala Ile Gly Phe Tyr
        210             215             220

Leu Leu Leu Lys Gly Leu Gly Val Asp Leu Leu Trp Thr Leu Glu Lys
225             230             235                     240

Ala Gln Arg Trp Cys Glu Gln Pro Glu Trp Val His Ile Asp Thr Thr
            245             250                 255

Pro Phe Ala Ser Leu Leu Lys Asn Leu Gly Thr Leu Phe Gly Leu Gly
            260             265             270

Leu Ala Leu Asn Ser Ser Met Tyr Arg Glu Ser Cys Lys Gly Lys Leu
            275             280             285

Ser Lys Trp Leu Pro Phe Arg Leu Ser Ser Ile Val Ala Ser Leu Val
        290             295             300

Leu Leu His Val Phe Asp Ser Leu Lys Pro Pro Ser Gln Val Glu Leu
305             310             315                     320

Val Phe Tyr Val Leu Ser Phe Cys Lys Ser Ala Val Val Pro Leu Ala
                325             330             335

Ser Val Ser Val Ile Pro Tyr Cys Leu Ala Gln Val Leu Gly Gln Pro
            340             345             350

His Lys Lys Ser Leu
            355
```